United States Patent
Chiba et al.

(10) Patent No.: US 9,606,138 B2
(45) Date of Patent: Mar. 28, 2017

(54) MOTION RECOGNITION APPARATUS, MOTION RECOGNITION SYSTEM, AND MOTION RECOGNITION METHOD

(71) Applicants: Yuki Chiba, Tokyo (JP); Yoji Miyazaki, Tokyo (JP)

(72) Inventors: Yuki Chiba, Tokyo (JP); Yoji Miyazaki, Tokyo (JP)

(73) Assignee: NEC CORPORATION, Tokyo (JP)

( * ) Notice: Subject to any disclaimer, the term of this patent is extended or adjusted under 35 U.S.C. 154(b) by 411 days.

(21) Appl. No.: 14/377,217

(22) PCT Filed: Jan. 21, 2013

(86) PCT No.: PCT/JP2013/051035
§ 371 (c)(1),
(2) Date: Aug. 7, 2014

(87) PCT Pub. No.: WO2013/128972
PCT Pub. Date: Sep. 6, 2013

(65) Prior Publication Data
US 2015/0006446 A1    Jan. 1, 2015

(30) Foreign Application Priority Data
Mar. 2, 2012    (JP) .............................. 2012-046610

(51) Int. Cl.
*G06F 15/18* (2006.01)
*G01P 13/00* (2006.01)
(Continued)

(52) U.S. Cl.
CPC ............ *G01P 13/00* (2013.01); *A61B 5/1116* (2013.01); *A61B 5/1123* (2013.01);
(Continued)

(58) Field of Classification Search
USPC ......................................................... 706/12
See application file for complete search history.

(56) References Cited

U.S. PATENT DOCUMENTS 7,799,703 B2 *  9/2010  Kubota .............. H01L 21/3105
                                          438/765
7,922,865 B2 *  4/2011  Miyata ............... H01J 37/3408
                                          156/345.42
(Continued)

FOREIGN PATENT DOCUMENTS

CN          1457246 A      11/2003
CN        101394787 A       3/2009
(Continued)

OTHER PUBLICATIONS

On the use of wearable sensors to enhance motion intention detection for a contralaterally controlled FES system Andrés F. Ruiz-Olaya 2016 IEEE 13th International Conference on Wearable and Implantable Body Sensor Networks (BSN) Year: 2016 pp. 324-328, DOI: 10.1109/BSN.2016.7516282 IEEE Conference Publications.*

(Continued)

*Primary Examiner* — Michael B Holmes

(57) ABSTRACT

Provided are a motion recognition apparatus, a motion recognition system and a motion recognition method that enable 'event motions' to be recognized with a small number of calculations. The motion recognition system, which recognizes user motions by using sensor data, is configured to be provided with: a cyclical loss detection means for detecting cyclical losses of sensor data when a user is moving; and a recognition processing means for setting data intervals to be used for recognizing motions in accordance with the cyclical losses of sensor data that were detected, and for recognizing user motions on the basis of sensor data for the data intervals that have been set.

20 Claims, 16 Drawing Sheets

(51) Int. Cl.
*A61B 5/11* (2006.01)
*G06N 99/00* (2010.01)
*A61B 5/00* (2006.01)

(52) U.S. Cl.
CPC ......... *A61B 5/7282* (2013.01); *G06N 99/005* (2013.01); *A61B 5/0022* (2013.01); *A61B 5/1117* (2013.01); *A61B 5/1118* (2013.01); *A61B 5/6898* (2013.01); *A61B 5/7264* (2013.01); *A61B 2562/0219* (2013.01)

(56) References Cited

U.S. PATENT DOCUMENTS

| | | | |
|---|---|---|---|
| 2006/0220882 | A1 | 10/2006 | Makino |
| 2010/0063419 | A1 | 3/2010 | Mostafavi |

FOREIGN PATENT DOCUMENTS

| | | | |
|---|---|---|---|
| CN | 101980659 | A | 2/2011 |
| CN | 102027440 | A | 4/2011 |
| JP | 2000-213967 | A | 8/2000 |
| JP | 2005-21450 | A | 1/2005 |
| JP | 2005-152633 | A | 6/2005 |
| JP | 2006-262973 | A | 10/2006 |
| JP | 2007-175225 | A | 7/2007 |
| JP | 2007-209430 | A | 8/2007 |
| JP | 2010-104396 | A | 5/2010 |
| JP | 2011-123832 | A | 6/2011 |
| JP | 2011-206274 | A | 10/2011 |
| WO | 2004/026138 | A1 | 4/2004 |

OTHER PUBLICATIONS

Interactive virtual 3D gallery using motion detection of mobile device C. Sinthanayothin; N. Wongwean; W. Bholsithi International Conference on Mobile IT Convergence Year: 2011 pp. 120-125 IEEE Conference Publications.*
A wearable sensor system for rehabilitation apllications Gautam Sadarangani; Carlo Menon 2015 IEEE International Conference on Rehabilitation Robotics (ICORR) Year: 2015 pp. 672-677, DOI: 10.1109/ICORR.2015.7281278 IEEE Conference Publications.*
Sensor sensitivity to posture transitions in a lower-extremity orthotic device Matthew Gawlik; Edward Sazonov; Xiangrong Shen SoutheastCon 2015 Year: 2015 pp. 1-5, DOI: 10.1109/SECON.2015.7132933 IEEE Conference Publications.*
Chinese Office Action for CN Application No. 201380012221.4 issued on Sep. 9, 2015 with English Translation.
Zuolei Sun et al: "Activity classification and dead reckoning for pedestrian navigation with wearable sensors", Measurement Science and Technology, IOP, Bristol, GB, vol. 20, No. 1, Jan. 1, 2009. p. 15203, Cited in EESR.
Jonghee Han et al: "Adaptive windowing for gait phase discrimination in Parkinsonian gait using 3-axis acceleration signals", Medical & Biological Engineering &Computing, Springer, Berlin, DE, vol. 47, No. 11, Aug. 20, 2009, pp. 1155-1164, Cited in EESR.
Extended European Search Report for EP Application No. EP13754172.8 mailed on Sep. 25, 2015.
International Search Report for PCT Application No. PCT/JP2013/051035, mailed on Feb. 12, 2013.

* cited by examiner

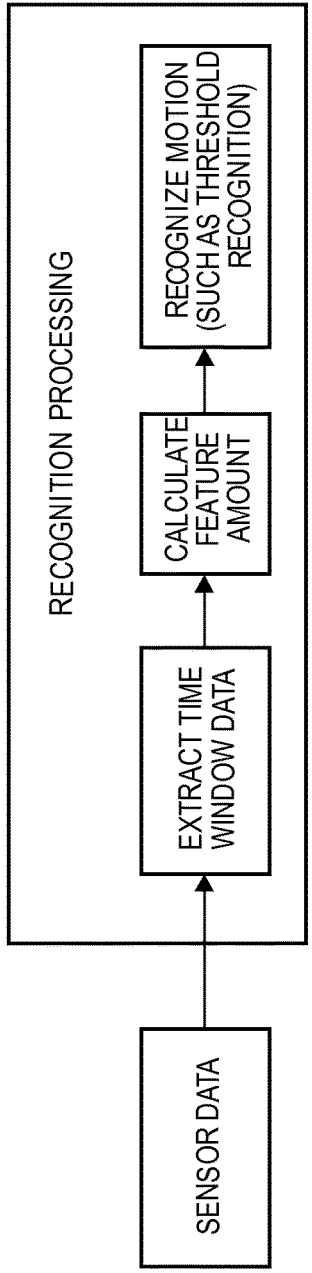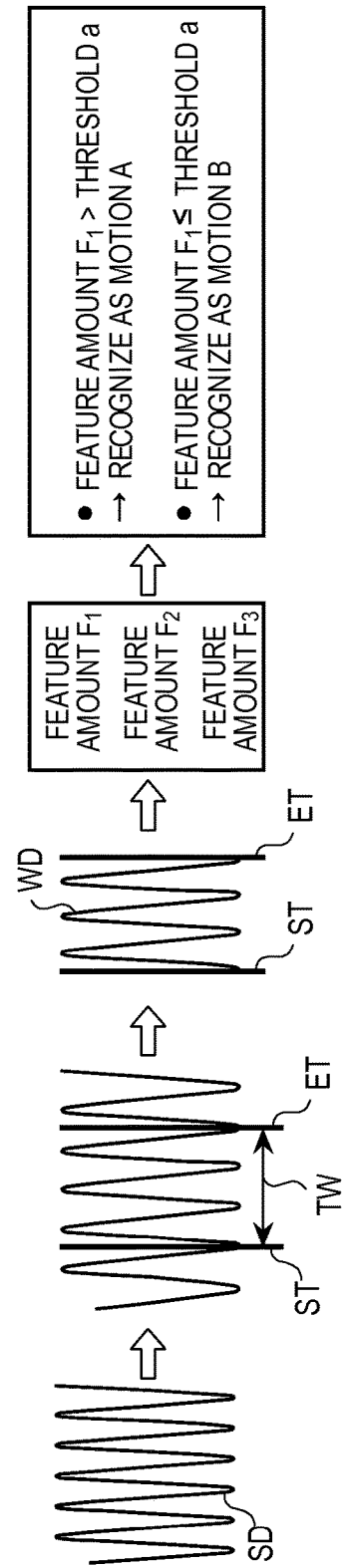

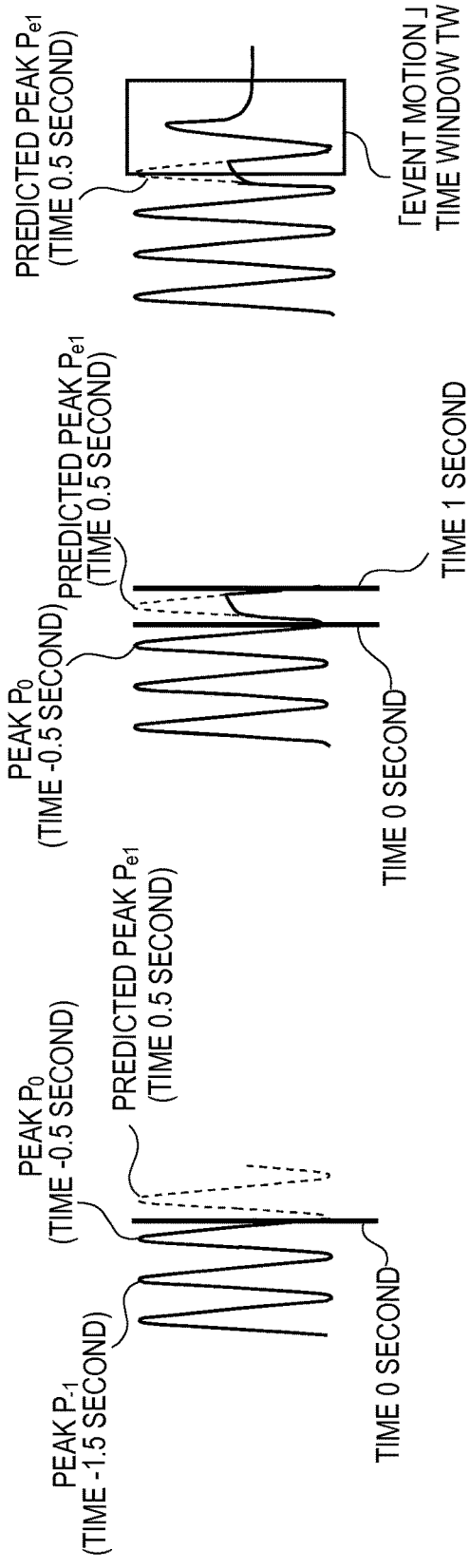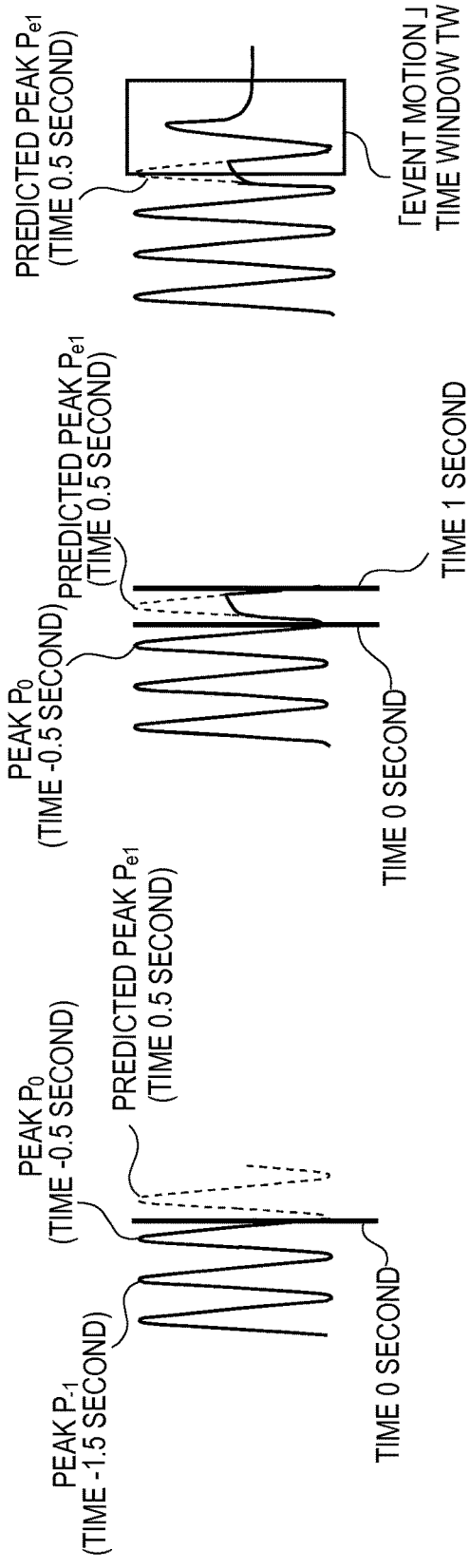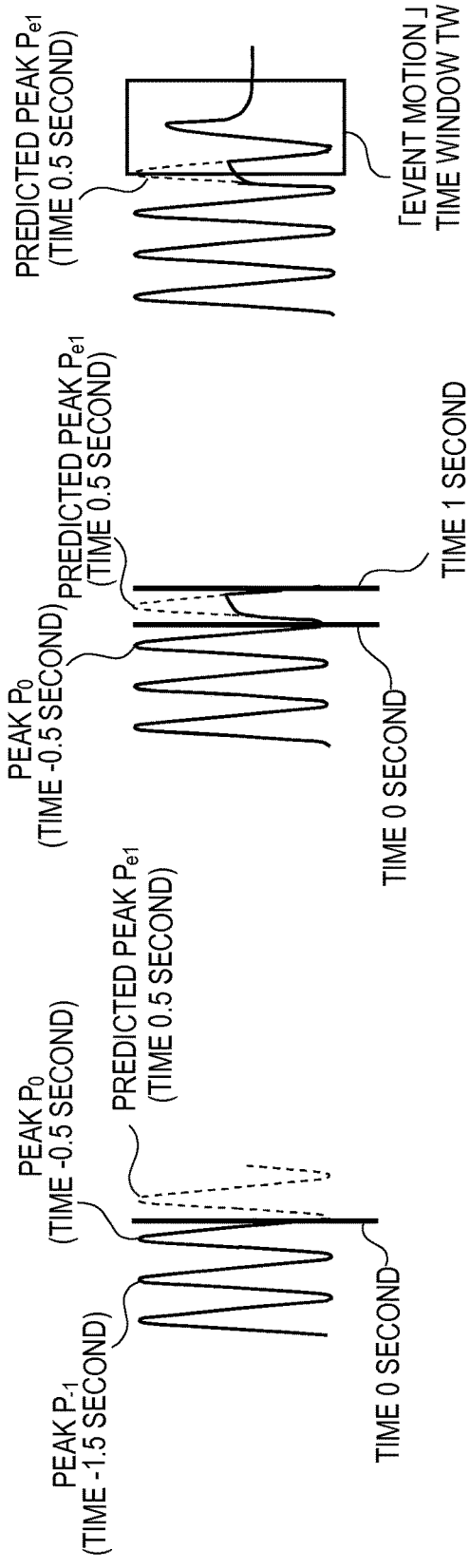

FIG.12

| PEAK | $P_{-300}$ | ... | $P_{-5}$ | $P_{-4}$ | $P_{-3}$ | $P_{-2}$ | $P_{-1}$ | $P_0$ |
|---|---|---|---|---|---|---|---|---|
| PEAK TIME (SECOND) | -311.1 | ... | -5.3 | -4.2 | -2.8 | -1.9 | -1.0 | 0.0 |
| PEAK INTERVAL | $PI_{-300}$ | ... | $PI_5$ | $PI_4$ | $PI_3$ | $PI_2$ | $PI_1$ | $PI_0$ |
| PEAK INTERVAL DURATION (SECOND) | - | ... | 1.2 | 1.1 | 1.4 | 0.9 | 0.9 | 1.0 |

MOTION RECOGNITION APPARATUS, MOTION RECOGNITION SYSTEM, AND MOTION RECOGNITION METHOD

This application is a National Stage Entry of PCT/JP2013/051035 filed on Jan. 21, 2013, which claims priority from Japanese Patent Application 2012-046610 filed on Mar. 2, 2012, the contents of all of which are incorporated herein by reference, in their entirety.

TECHNICAL FIELD

The present invention relates to a motion recognition apparatus, a motion recognition system and a motion recognition method.

BACKGROUND ART

In recent years, trials to recognize motions of users using various sensors are popularly made. FIG. 1A illustrates a flow of common motion recognition processing using a sensor. First, data of a certain section (referred to as a "time window" below) is extracted from items of continuous sensor data. Next, a statistical amount (referred to as a "feature amount") or the like which indicates a feature of a motion to be recognized is calculated from the extracted time window data. Further, the type of the motion is determined by checking whether or not the calculated feature amount is larger than, for example, a threshold set in advance by way of comparison and using a pattern recognition method. Hereinafter, performing three types of processing of data extraction, feature amount calculation and motion recognition is collectively referred to as "recognition processing".

FIG. 1B illustrates recognition processing when, for example, sensor data SD obtained from an acceleration sensor upon "walking" is used. Data WD of a time window TW specified based on a start time ST and an end time ET is extracted from the sensor data SD. For example, feature amounts $F_1$, $F_2$ and $F_3$ are calculated from the extracted data WD. The motion is recognized as a motion A when the calculated feature amount F1 is larger than a threshold a, and is recognized as a motion B when the feature amount F1 is smaller than the threshold a. FIG. 2 illustrates a configuration example of a motion recognizing system which realizes this recognition processing.

In FIG. 2, a sensor data acquiring/storage unit 1 acquires data from a sensor and temporarily stores the data. A time window start/end time setting unit 21 sets a start time and an end time of a time window which is a section from which data is extracted. A time window data extracting unit 22 extracts sensor data of the set time window. A feature amount calculating unit 23 calculates a feature amount of the extracted sensor data. A motion recognizing unit 24 recognizes a motion based on the calculated feature amount.

Patent Literature 1 discloses an example of recognizing a motion using a sensor in this way. Patent Literature 1 discloses performing recognition processing in order of time window setting, data extraction, feature amount calculation and motion recognition using acceleration sensors attached to a person.

CITATION LIST

Patent Literature

{PTL 1} JP-A-2011-123832

SUMMARY OF INVENTION

Technical Problem

However, the method disclosed in Patent Literature 1 has a problem that a calculation amount increases when a motion such as "stand up" or "sit" which is finished in a short time of about 1 second to 5 seconds is recognized without detection failure. The reason will be described below.

First, FIG. 3 illustrates that time window data is extracted from sensor data upon recognition of a repeatable motion such as "walk". FIG. 3A illustrates a range of a start SP to an end EP of a motion of one step in the sensor data SD of "walk", that is, a range UP of one cycle. Generally, time window data to be extracted needs to include data of one cycle of a motion of interest, that is, data of a start to an end of a motion. When one step is estimated as about 1 second, the time window TW requires the duration of 1 second or more. Hence, in examples in FIGS. 3B, 3C and 3D, the duration of the time window TW is set to 3 seconds. FIGS. 3B, 3C and 3D illustrate three examples (ST1, ST2 and ST3) of start times (timings) ST of a time window which are shifted. A repeatable motion such as "walk" frequently continues for a comparatively long time such as several 10 seconds to 1 minute or more, so that it is possible to correctly determine any time window of a "timing 1", a "timing 2" or a "timing 3" illustrated in FIGS. 3B, 3C and 3D likewise. That is, when the motion continues for a common motion continuation time of several 10 seconds to 1 minute or more, even if a repetition interval of neighboring time windows, that is, an interval between start times (ST1, ST2 and ST3) of neighboring time windows is set long, the likelihood that detection failure occurs is low and it is possible to correctly recognize a motion.

Hence, a specific time window setting method includes, for example, a method of setting a data point obtained immediately after an end time ET of a given time window to a start time ST of a next time window to prevent a blank section in which the time window TW is not set from being produced in the obtained time-series data, and a method of setting an interval between time windows such that data sections which are half a time window duration overlaps between neighboring time windows.

Next, FIG. 4 illustrates that time window data is extracted from the sensor data SD upon recognition of a motion such as "stand up" or "sit" which is finished in a short time of about 1 second to 5 seconds. FIG. 4A illustrates a range of a start SP to an end EP of a "sit" motion, that is, a range UP of one cycle. Such a motion which is finished in a short time is referred to as an "event motion" in this description. FIGS. 4B, 4C and 4D illustrate three examples (ST1, ST2 and ST3) of start times (timings) of a time window which are shifted. Even upon the "event motion", a section UP of the start SP to the end EP of the motion needs to be settled in the time window TW as in a "timing 2" illustrated in FIG. 4C similar to the repeatable motion such as the "walk" motion. However, the "event motion" is finished in a short time, and, when a time interval between neighboring time windows is set long, a time window does not include one cycle of a motion or more and therefore cannot be correctly set as in a "timing 1" illustrated in FIG. 4B and a "timing 3" illustrated in FIG. 4D.

Hence, to settle a start to an end of a motion in a time window upon "event motion" recognition, it is necessary to set a repetition interval between neighboring time windows short and repeatedly execute processing of data extraction, feature amount calculation and motion recognition in each time window as illustrated in FIG. 5. FIG. 5 illustrates an example of recognizing a "sit" event motion, and illustrates that recognition processing is repeatedly executed in a plurality of a time window 1, a time window 2, a time window 3, a time window 4 and so on of slightly different start times ST. As a result, recognition processing in each time window is frequently performed, and therefore the number of times of the recognition processing increases and a great calculation amount is required. Further, when recognition processing is performed using a device such as a mobile telephone which has only limited calculation resources, there are problems that processing requires a time and power consumption of a battery is significant.

It is therefore an object of the present invention to provide a motion recognizing apparatus, a motion recognizing system and a motion recognizing method which can solve the above problems and can recognize an "event motion" with a small calculation amount.

Solution to Problem

To achieve the above object, a motion recognizing apparatus according to the present invention is a motion recognizing apparatus which recognizes a motion of a user using sensor data, and has: a cyclicity loss detecting means which detects loss of cyclicity of the sensor data when the user is making the motion; and a recognition processing means which sets a data section used for motion recognition according to the detected loss of the cyclicity of the sensor data, and recognizes the motion of the user based on the sensor data of the data section.

Further, a motion recognizing system according to the present invention has: the motion recognizing apparatus; a sensor data acquiring/storage unit which acquires sensor data outputted from a sensor and temporarily stores the sensor data; and a recognition result output unit which outputs a result of motion recognition performed by the recognition processing unit.

Furthermore, a motion recognizing method according to the present invention is a motion recognizing method of recognizing a motion of a user using sensor data, and includes: a step of detecting loss of cyclicity of the sensor data when the user is making the motion; and a step of setting a data section used for motion recognition according to the detected loss of the cyclicity of the sensor data, and recognizing the motion of the user based on the sensor data of the data section.

Advantages Effects of the Invention

An effect of the present invention is to reduce a calculation amount in processing of recognizing an "event motion".

BRIEF DESCRIPTION OF DRAWINGS

FIG. 1 A figure illustrates a view illustrating a flow of common motion recognition processing.

FIG. 7 A figure illustrates a diagram illustrating specific processing according to the first embodiment of the present invention.

FIG. 12 A figure illustrates a view illustrating an example of a peak interval and peak information stored in a peak interval history storage unit 35 according to the second embodiment of the present invention.

DESCRIPTION OF EMBODIMENTS

Next, a first embodiment of the present invention will be described in details with reference to FIGS. 6 to 10.

Figure 6:
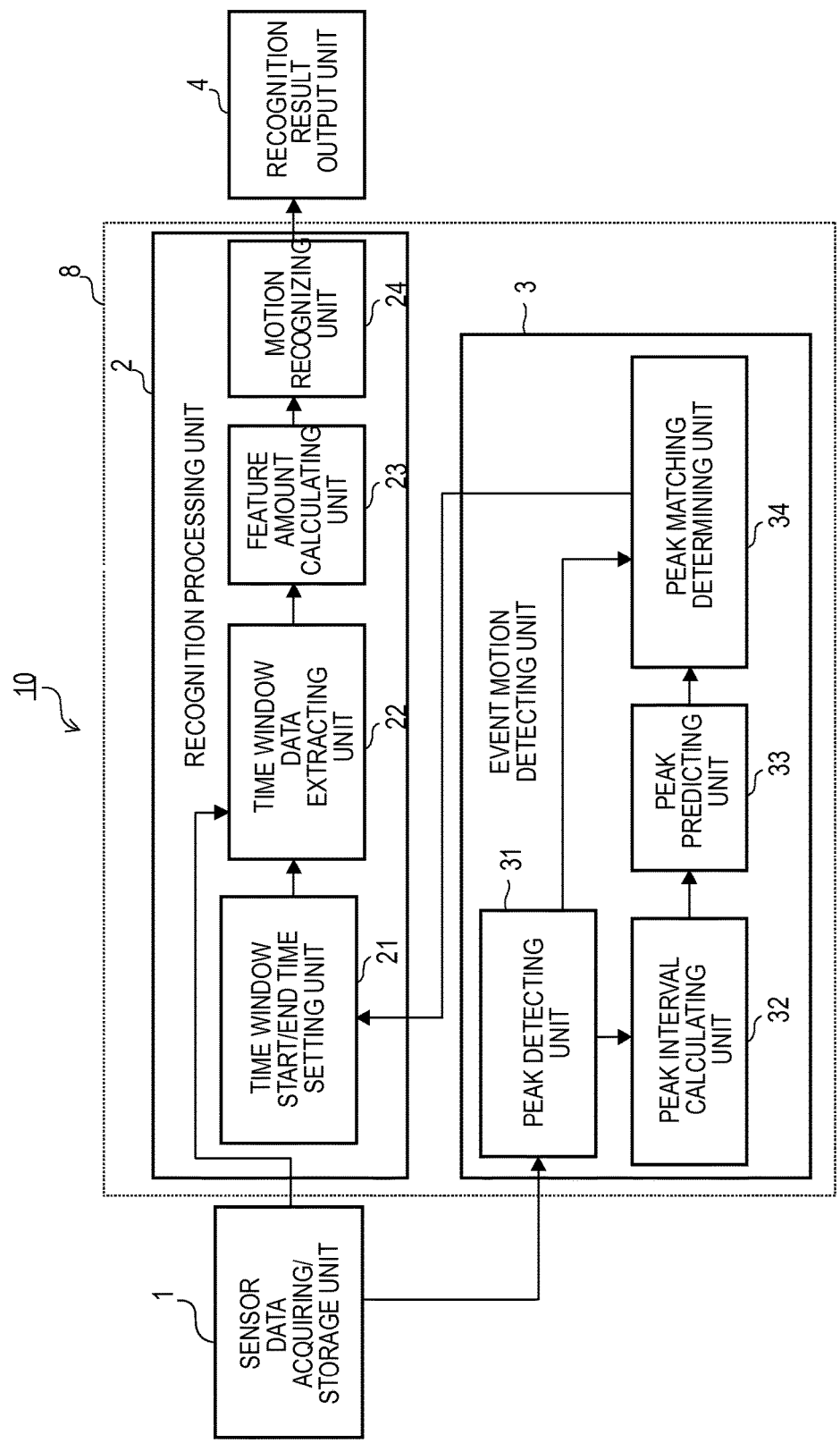
FIG. 6 A figure illustrates a block diagram illustrating a configuration according to a first embodiment of the present invention.

FIG. 6 illustrates a motion recognizing system 10 according to the first embodiment of the present invention. The motion recognizing system 10 has a sensor data acquiring/storage unit 1, a recognition processing unit 2, an event motion detecting unit 3 and a recognition result output unit 4. The recognition processing unit 2 has a time window start/end time setting unit 21, a time window data extracting unit 22, a feature amount calculating unit 23 and a motion recognizing unit 24. The event motion detecting unit 3 has a peak detecting unit 31, a peak interval calculating unit 32, a peak predicting unit 33 and a peak matching determining unit 34. The recognition processing unit 2 and the event operation detecting unit 3 may configure a motion recognizing apparatus 8. The event motion detecting unit 3 is also referred to as a cyclicity loss detecting means.

The sensor data acquiring/storage unit 1 acquires sensor data which represents a motion of a user from various sensors, and temporarily stores the sensor data. The peak detecting unit 31 detects a time (referred to as a peak time below) of at least a top of a peak shape of the sensor data obtained by the sensor data acquiring/storage unit 1. The peak interval calculating unit 32 calculates an interval between the peak times detected by the peak detecting unit 31. The peak predicting unit 33 predicts a peak time which appears next from a value of the peak interval calculated by the peak interval calculating unit 32 and an obtained time of the latest peak. The peak matching determining unit 34 compares the peak time detected by the peak detecting unit 31 and the peak time predicted by the peak predicting unit 33, and determines whether or not a gap between the times is in a predetermined certain time duration.

The time window start/end time setting unit 21 sets a time window start time and end time to settle in the time window the time at which an "event motion" occurs only when the event motion detecting unit 3 detects an occurrence of the "event motion". The time window data extracting unit 22 clips sensor data of a time window having a predetermined duration from the time window start time and end time set by the time window start/end time setting unit 21. The feature amount calculating unit 23 calculates a feature amount which represents a feature of a recognition target motion using the time window data clipped by the time window data extracting unit 22. The feature amount calculating unit 23 determines whether an estimation target motion is performed using the feature amount calculated by the feature amount calculating unit 23.

When there is a plurality of types of recognition target motions, the recognition processing unit 2 may be configured to be separately prepared per target motion. When, for example, two types of motions of a "walk" motion and a "sit down" motion are recognized, a configuration including two recognition processing units of a "walk" recognition processing unit and a "sit" recognition processing unit may also be employed.

When motion recognition is performed targeting at a plurality of motions in this way, each motion is recognized in advance as a motion which belongs to an "event motion" or as a motion which does not belong to the "event motion" and is stored in the recognition processing unit of each motion. When, for example, four types of motions of "walk", "run", "stand up" and "sit down" are recognized, "walk" is not recognized as an "event motion", "run" is not recognized as the "event motion", "stand up" is recognized as the "event motion" and "sit down" is recognized as the "event motion" and these motions are stored in the recognition processing unit 2.

Figure 2:
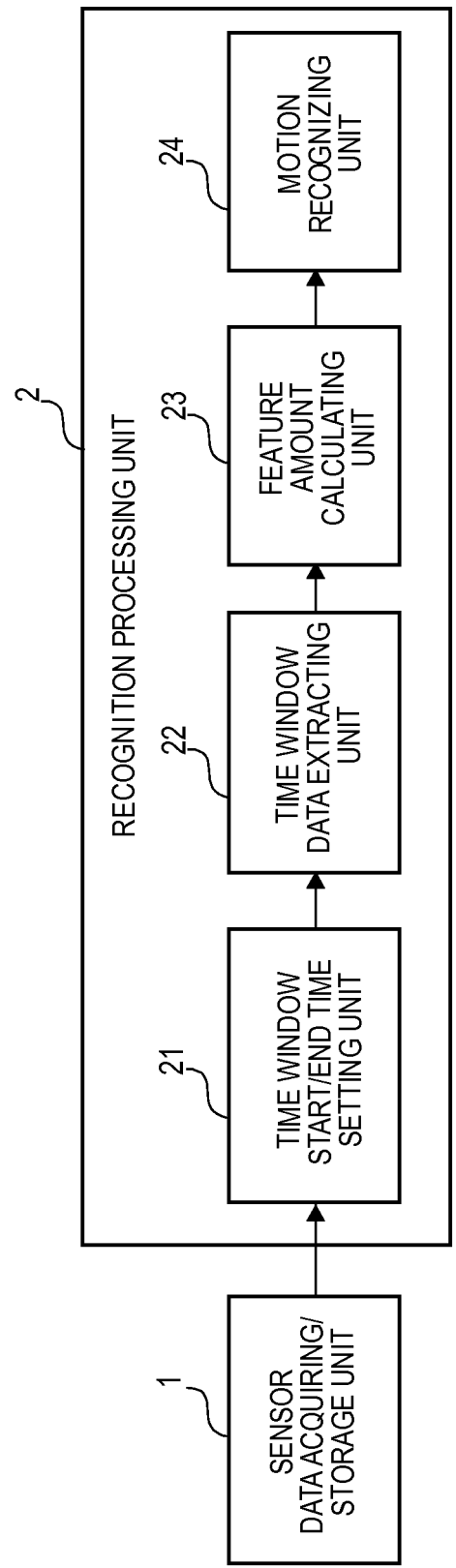
FIG. 2 A figure illustrates a block diagram illustrating a configuration of a motion recognizing system used in the motion recognition processing in FIG. 1.
Figure 3:
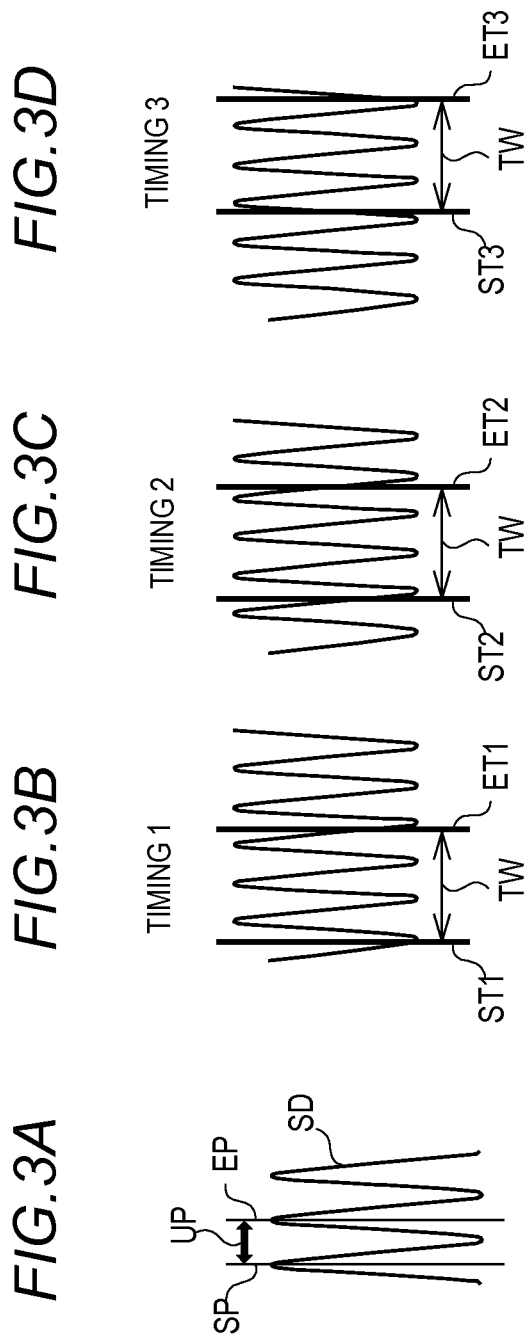
FIG. 3 A figure illustrates a view illustrating a relationship between a time window start/end time and a start/end of a motion upon recognition of a repeatable motion such as "walk".
Figure 4:
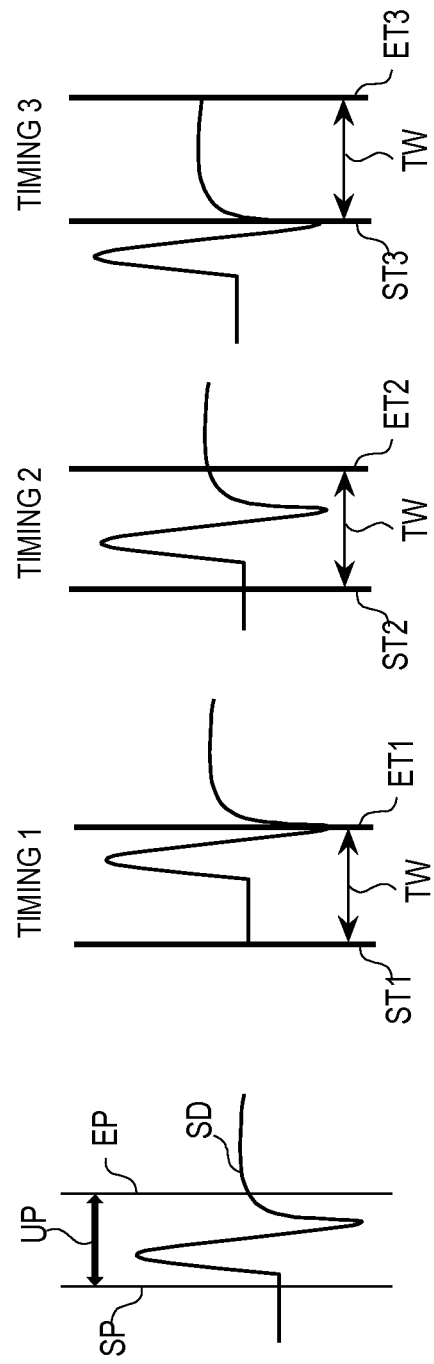
FIG. 4 A figure illustrates a view illustrating a relationship between a time window start/end time and a start/end of a motion upon recognition of an "event motion".

Further, only when the event motion detecting unit 3 detects an occurrence of the "event motion", the recognition processing unit of the "event motion" executes recognition processing. Meanwhile, recognition processing used in a relevant technique as illustrated in FIG. 2 may be performed as processing of recognizing a motion which is not an "event motion" without using the event motion detecting unit 3.

The motion recognizing system 10 is, for example, a mobile telephone of the user although the motion recognizing system 10 is not limited thereto as a physical configuration. In this case, when, for example, the user possesses a mobile telephone on which an acceleration sensor is mounted, the sensor data acquiring/storage unit 1 of the motion recognizing unit 10 inside the mobile telephone acquires sensor data generated by the acceleration sensor. Each processing is executed in the event motion detecting unit 3 and the recognition processing unit 2 using the obtained acceleration sensor data, and a recognition result obtained by the motion recognizing unit 24 of the recognition processing unit 2 is displayed on the recognition result output unit 4 which is a display device of a mobile telephone.

The "walk" motion which is not the "event motion" and the "sit" motion which is the "event motion" will be described as a specific example according to the first embodiment per component based on a processing flow. A case will be described where the sensor data acquiring/storage unit 1 acquires acceleration data which is an example of sensor data in real time, and sequentially processes the acquired acceleration data.

First, the sensor data acquiring/storage unit 1 acquires sensor data outputted from a sensor when a user is making a motion. Further, sensor data of a short time corresponding to predetermined time duration such as about several seconds to several tens of seconds is temporarily stored. The sensor data acquiring/storage unit 1 inputs the obtained sensor data to the peak detecting unit 31 of the event motion detecting unit 3. When, for example, the sensor data acquiring/storage unit 1 is provided in a mobile telephone terminal on which the acceleration sensor is mounted, it is possible to obtain acceleration sensor data when the user is making a motion since the user carries the mobile telephone.

The peak detecting unit 31 detects a peak in the sensor data obtained from the sensor data acquiring/storage unit 1. The peak refers to at least a data point which is a local maximum or a data point which is a local minimum when a value of sensor data is read in a chronological order. The peak detecting unit 31 supplies "peak information" which includes a peak time of the detected peak, to the peak interval calculating unit 32 and the peak matching determining unit 34.

The "peak information" includes at least time information of a data point of a peak. Other pieces of peak information include, for example, a value of data of a data point which is a peak and a value of an inclination between the data point which is the peak and data points prior to and subsequent to this data point.

The peak detection processing is repeatedly executed by the peak detecting unit 31 every time sensor data of a predetermined time is obtained, and new peak information is supplied to the peak interval calculating unit 32 and the peak matching determining unit 34 every time the new peak information is obtained. Further, when there is no peak in the obtained sensor data, the peak detecting unit 31 does not supply peak information to the peak interval calculating unit 32 and the peak matching determining unit 34.

A reference to FIG. 7A will be made to continue explanation. FIG. 7A schematically illustrates sensor data of a "walk" motion obtained from the acceleration sensor attached to the user. As illustrated in FIG. 7A, a case will be described where sensor data of a given time to time 0 second is obtained. The peak detecting unit 31 detects a peak $P_0$ at time −0.5 second, and supplies information of the obtained peak information as peak information to the peak interval calculating unit 32 and the peak matching determining unit 34. Further, before sensor data of the given time to time 0 second is obtained, a peak $P_{-1}$ has already been detected at time −1.5 second and peak information of the peak $P_{-1}$ has already been supplied to the peak interval calculating unit 32.

Further, although an example of a peak is a data point which is a local maximum or a data point which is a local minimum as described above, a peak to be detected is not limited to this. A peak is, for example, a point which is a local maximum and a maximum value in a certain data section or a point which is a local minimum and a value in a specific range. Further, when multiple peaks which satisfy a condition are detected in a certain data section, only a peak which represents cyclicity of a motion may be detected by using a rule that only a peak having the highest value among detected peaks is regarded as a peak.

The peak interval calculating unit 32 calculates a time interval between the temporally latest peak and the second latest peak compared to the latest peak, and supplies a value of the calculated peak interval and peak information of the latest peak to the peak predicting unit 33.

An example of FIG. 7A will be described, and the peak interval calculating unit 32 calculates a time interval $PI_0$ between the latest peak $P_0$ (time −0.5 second) and the second latest peak $P_{-1}$ (time −1.5 second) compared to the latest peak, and obtains a result of (−0.5 second)−(−1.5 second)=1 second. The peak interval calculating unit 32 supplies a value of 1 second of the calculated peak interval and time information of −0.5 second which is peak information of the peak $P_0$ to the peak predicting unit 33.

The peak predicting unit 33 predicts a peak which appears the next using the peak interval and the temporally latest peak information obtained from the peak interval calculating unit 32. Next, an example of a method of predicting a peak will be described using FIGS. 7 and 8.

FIGS. 7A and 8 schematically illustrate sensor data of the "walk" motion obtained from the acceleration sensor attached to the user as described above. In case of the "walk" motion, a section between a given peak and a next peak corresponds to one step of "walk", that is, one cycle of a motion. When the "walk" motion cyclically continues at a certain pace, a peak interval is thought to be fixed. Hence, as illustrated in FIG. 7A, a predicted peak $P_{e1}$ is predicted to appear after the immediate peak interval $PI_0$ passes after the latest peak $P_0$ appears.

Figure 8B:
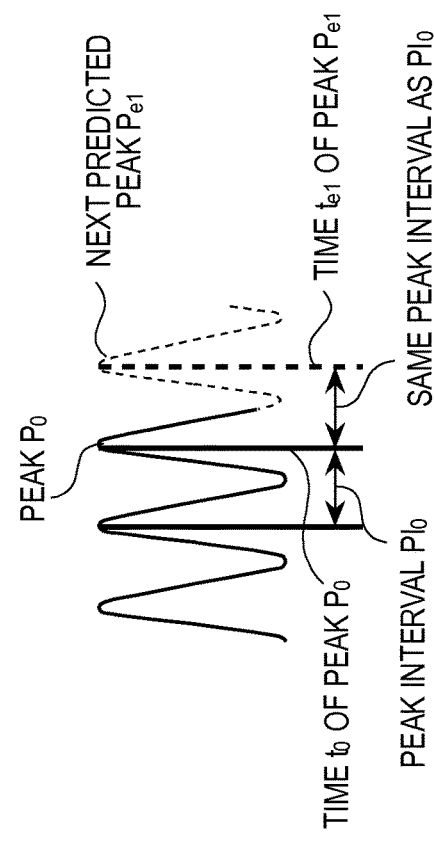
FIG. 8 A figure illustrates an example of a method of predicting a peak which appears next using immediate peak information.
Figure 8A:
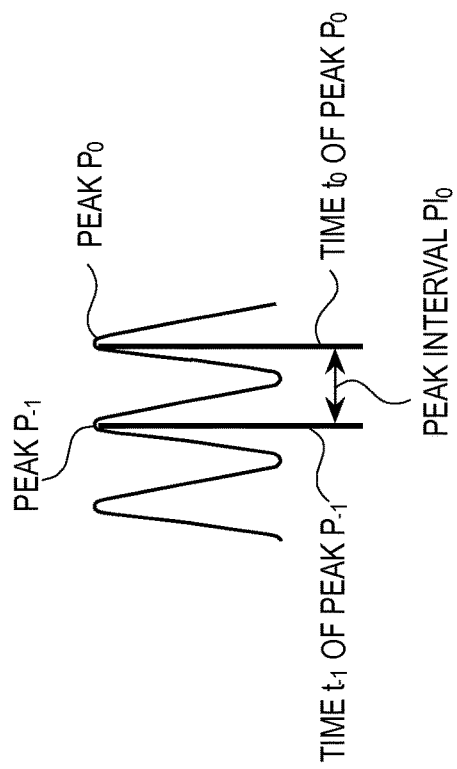

As illustrated in FIG. 8A, this peak interval $PI_0$ is a difference between a time $t_0$ of a peak $P_0$ and a time $t_{-1}$ of a peak $P_{-1}$, and is 1 second in this case described above. Hence, as illustrated in FIG. 8B, a next peak is thought to appear at a time $t_{e1}$ (0.5 second) obtained by adding a value (1 second) of the immediate peak interval $PI_0$ to time $t_0$ (−0.5 second) of the latest peak $P_0$. The peak predicting unit 33 supplies predicted peak information to the peak matching determining unit 34. The "predicted peak information" includes at least a value (0.5 second) of time $t_{e1}$ of a peak to be predicted.

The peak matching determining unit 34 compares the predicted peak information obtained from the peak predicting unit 33 and peak information obtained from the sensor data by the peak detecting unit 31, and checks whether or not the two pieces of peak information match. Whether or not the predicted peak and a peak of a new time (referred to as a new peak) instead of the peak obtained from the peak detecting unit 31 by the peak interval calculating unit 32 and the peak predicting unit 33 is checked.

Figure 9A:
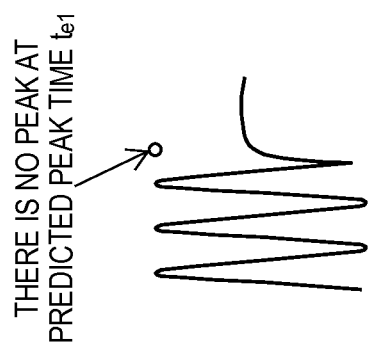
FIG. 9 A figure illustrates a view for explaining whether or not a predicted peak and a peak actually obtained match.
Figure 9B:
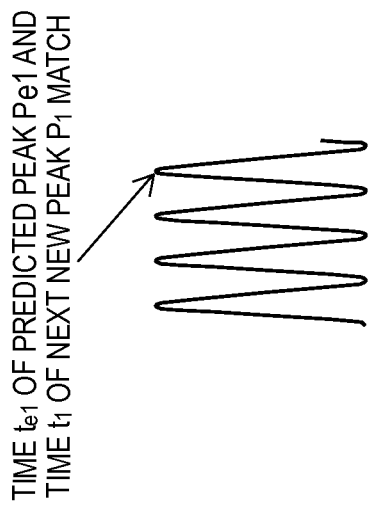
Figure 9C:
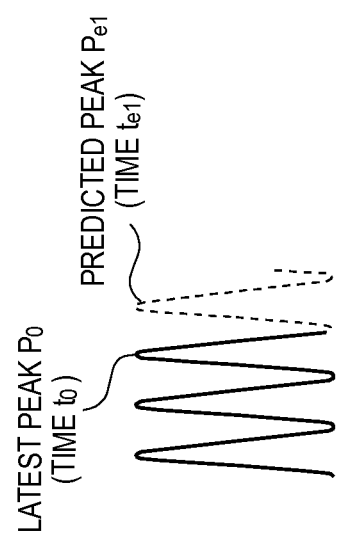

Meanwhile, a method of determining whether or not peaks match will be described using FIG. 9. FIG. 9A illustrates that the peak $P_{e1}$ (time $t_{e1}$) which is about to appear next to the latest peak $P_0$ (time $t_0$). FIG. 9B illustrates that the predicted peak $P_{e1}$ and the new peak $P_1$ match. FIG. 9C illustrates that the predicted peak and the new peak do not match.

Given that, for example, only an occurrence time of a peak is used as peak information, when a difference between the occurrence time $t_{e1}$ of the predicted peak $P_{e1}$ obtained from the peak predicting unit 33 and the occurrence time $t_1$ of the new peak $P_1$ obtained from the peak detecting unit 31 is smaller than a predetermined value (FIG. 9B), it is recognized that the predicted peak and the new peak match. When the peaks match, the peak matching determining unit 34 supplies a recognition result that the peaks match, that is, a recognition result that a cyclic motion continues, predicted peak information and new peak information to the time window start/end time setting unit 21.

Further, when a peak does not actually appear at time $t_{e1}$ of the predicted peak (FIG. 9C) and, more specifically, the difference between the occurrence time $t_{e1}$ of the predicted peak obtained from the peak predicting unit 33 and the occurrence time $t_1$ of the new peak obtained from the peak detecting unit 31 is larger than a predetermined value, it is recognized that the predicted peak and the new peak do not match.

When the peaks do not match, the peak matching determining unit 34 supplies a recognition result that the peaks do not match, that is, the recognition result that a cyclic motion stops halfway and an "event motion" occurs, predicted peak information and new peak information to the time window start/end time setting unit 21.

Further, even when the peak detecting unit 31 detects the peak used by the peak interval calculating unit 32 and the peak predicting unit 33 and then does not detect a new peak for predetermined time duration or more, a recognition result that the peaks do not match and predicted peak information may be supplied to the time window start/end time setting unit 21 likewise.

A case when peaks do not match will be described with reference to FIG. 7B. FIG. 7B illustrates that the sensor data acquiring/storage unit 1 obtains acceleration data of time 0 second to time 1 second, and the peak detecting unit 31 processes the acceleration data of time 0 second to time 1 second and does not detect a peak as a result. There is not actually a peak at time 0.5 second of the predicted peak $P_{e1}$, and therefore it is recognized that the predicted peak and the new peak do not match. Hence, a recognition result that the "event motion" occurs and time information of 0.5 second which is predicted peak information are supplied to the time window start/end time setting unit 21.

The time window start/end time setting unit 21 sets a time window start time and a time window end time according to the recognition result supplied from the peak matching determining unit 34.

More specifically, when the peak matching determining unit 34 determines that the "event motion" does not occur, the time window start/end time setting unit 21 does not set a time window related to "event motion" recognition and then the recognition processing unit 2 does not execute subsequent "event motion" recognition processing, either.

Further, when the peak matching determining unit 34 determines that the "event motion" occurs, the time window start time and end time of the "event motion" are set and subsequent recognition processing in the recognition processing unit 2 is executed.

When a plurality of motions is a recognition target, a configuration to prepare separate recognition processing units 2 and make recognition may be employed. In this regard, each recognition processing unit 2 stores in advance whether or not a recognition target motion is an "event motion". When, for example, a "walk" recognition processing unit 2a and a "stand up" recognition processing unit 2b are used as the recognition processing units 2, the "walk" recognition processing unit 2a stores in advance that a motion is not an "event motion" and the "stand up" recognition processing unit 2b stores in advance that a motion is an "event motion" to determine whether or not to execute processing of setting time window start/end times according to the recognition result of the peak matching determining unit 34.

Meanwhile, a specific time window setting method will be described. First, time window duration is set in advance per recognition target motion. Generally, data of the time window duration which is one cycle of a motion or a start to an end of a motion needs to be included in each time window.

For example, a case will be described where time window duration used to recognize "walk" is determined. In this case, for example, a motion of moving one step forward can be regarded as one cycle of the "walk" motion. A time required to make a motion of one step is estimated as about one second at maximum from a result of a conducted experiment and, consequently, the time window duration can be determined as 1 second.

Similarly, when a time window duration used to recognize a "sit" motion as an example of an "event motion" is taken into account, the time required to make a "sit" motion is estimated as about 2 seconds at maximum from a result of a conducted experiment and, consequently, the time window duration can be determined as 2 seconds.

Next, a specific setting method of time window start/end times of an "event motion" will be described. The method of setting the time window start time and end time of the "event motion" includes, for example, a method of setting a start time and an end time to set the peak time predicted by the peak predicting unit 33 as the time window start time, or a method of setting a start time and an end time to set the peak time predicted by the peak predicting unit 33 as a time window center time.

Another method is a method of setting a detected new peak time as a time window end time when the new peak is detected at a time different from the peak time predicted by the peak predicting unit 33. When the new peak time is set as the time window end time, a time found by tracking predetermined time window duration from the set time window end time per motion of interest is set as a time window start time.

Similarly, for example, a method of setting the time of the new peak detected by the peak detecting unit 31 as the time window start time of the "event motion" is applicable.

Figure 5:
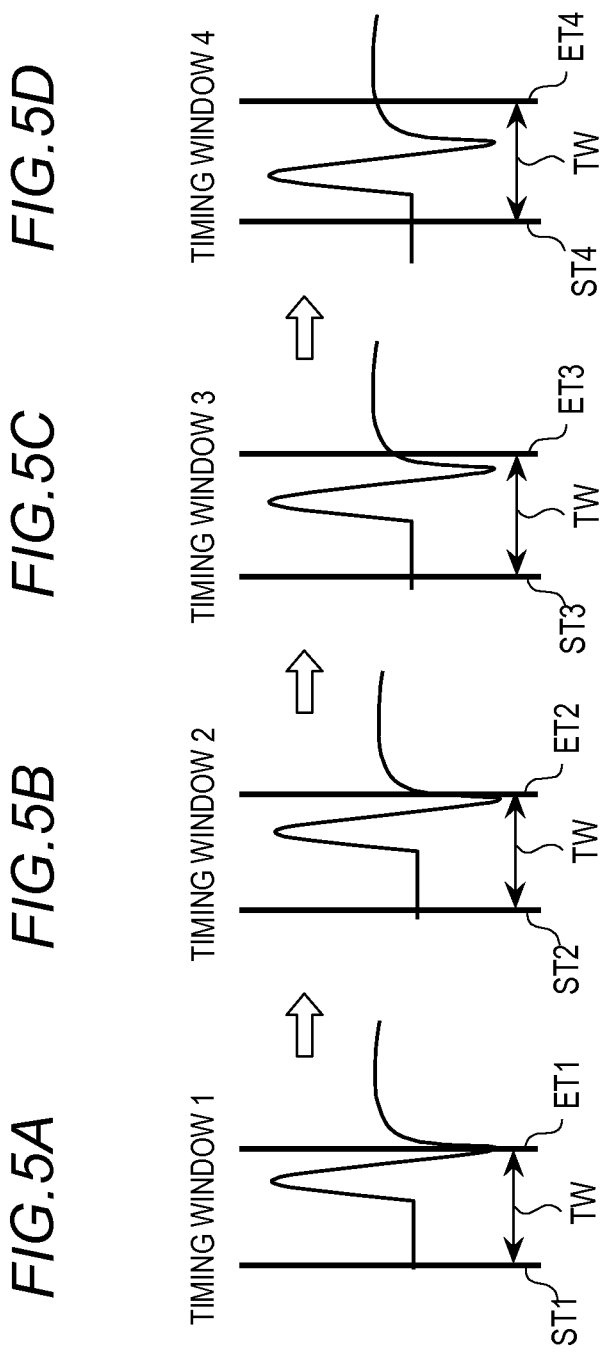
FIG. 5 A figure illustrates an explanatory diagram when recognition processing is repeated by shifting a time window start time a little by little in the "event motion" recognition processing.

A method of setting a plurality of time windows is also applicable. That is, a method of setting the time window according to the above method, setting a plurality of time windows set by shifting start and end times by a short time as illustrated in FIG. 5 only in certain sections prior to or subsequent to the set time window and executing recognition processing per time window is also applicable. In this regard, a method of using predetermined time duration by setting the preceding and subsequent sections to shift a time window, as sections of 6 seconds in total which are the preceding and subsequent sections of 3 seconds based on the set time window center time is applicable.

Another method of setting sections to shift a time window may be a method of separately setting sections to shift a time window per motion by, for example, setting sections as sections of 2 w seconds in total which are preceding and subsequent sections of w seconds based on the set time window center time when, for example, the time window duration is w seconds since the time window duration differs per motion to be recognized. The time window start/end time setting unit 21 supplies information of the time window start time and end time per motion to the time window data extracting unit 22.

Next, recognizing a "sit" motion will be specifically described with reference to FIG. 7C. As described above, using a method of setting a start time and an end time to set "sit" time window duration as 2 seconds and setting the peak time predicted by the peak predicting unit 22 as the start time of the time window will be described. The time window start/end time setting unit 21 obtains information of time 0.5 second of the predicted peak $P_{e1}$ as predicted peak information from the peak matching determining unit 34, and then sets the time window TW of 2 seconds of duration whose time window start point is 0.5 second of a predicted peak time.

The time window data extracting unit 22 clips sensor data from the sensor data temporarily stored in the sensor data acquiring/storage unit 1 according to the time window start time and end time of each motion obtained from the time window start/end time setting unit 21.

The time window extracting unit 22 supplies the clipped sensor data to the feature amount calculating unit 23.

The feature amount calculating unit 23 calculates a feature amount which characterizes a motion per recognition target motion using the sensor data obtained by the time window data extracting unit 22. The feature amount is thought to be, for example, various statistics amounts such as an average value or a variance value of sensor data of a time window, a maximum value or a minimum value. The feature amount calculating unit 23 supplies the obtained feature amount to the motion recognizing unit 24.

The motion recognizing unit 24 recognizes a motion at a time at which the time window is set using the feature amount obtained from the feature amount calculating unit 23. When, for example, a variance value in a time window is used as the feature amount to recognize a "walk" motion, motion recognition is performed using a rule to determine that the motion is "not walk" when the variance value is less than 4000 [$mG^2$] and the motion is "walk" when the variance value is 4000 [$mG^2$] or more. A motion recognition result obtained by the above processing is displayed on, for example, the display device of the mobile telephone which is the recognition result output unit 4.

The above processing of the time window data extracting unit 22, the feature amount calculating unit 23 and the motion recognizing unit 4 can use the method of the relevant technique, and can be used commonly for an "event motion" and a motion "other than the event motion".

Further, although a case has been described above where the peak predicting unit 33 predicts only a time of a peak which appears next using only time information of the peak, processing of predicting a more correct peak using a degree of a value of a data point which is a peak as peak information or a value of an inclination of the data point which is the peak and preceding and subsequent data points may also be performed. When, for example, a degree of a value is used as peak information in addition to the time, a method of predicting the time of the peak which appears next and supplying a value of the peak obtained from the peak interval calculating unit 32 as a predicted value of the value of the peak which appears next to the peak matching unit 34 is applicable.

Further, another method of predicting a peak may also be a method of predicting a time which has certain time duration without uniformly determining a time at which a peak appears. More specifically, when, for example, the peak interval calculated by the peak interval calculating unit 32 is $PI_0$ (second), an occurrence time of a predicted peak is a center time, a section which has duration of $PI_0/2$ (second) prior to and subsequent to this time is set as a predicted peak occurrence time. The peak matching determining unit 34 determines whether or not the peaks match depending on whether or not there is a new peak obtained from the peak detecting unit 31 in this predicted peak occurrence section.

Thus, the method which the peak matching determining unit 34 uses to determine whether or not peaks match in a predicted peak occurrence section having certain time duration is not limited to the above methods.

Additionally, for example, a method of assuming a Gaussian distribution in a predicted peak occurrence section, and determining whether or not peaks match depending on whether or not the new peak obtained from the peak detecting unit 31 is distributed in a predetermined range such as 30% or less of the entire distribution based on the center of the Gaussian distribution is applicable. Further, a method of predicting a peak with certain duration in this way is applicable not only to time duration but also to prediction of another peak information such as a degree of a value of a data point which is a peak.

In addition to the above, although a case has been described above where whether or not to execute "event motion" recognition processing depending on whether or not occurrence of an "event motion" is detected is determined, the same method is also applicable to motions other than the "event motion". That is, a rule that, when the event motion detecting unit 3 determines that the "event motion" does not occur, processing of recognizing a motion which is not the "event motion" is executed and, when the event motion detecting unit 3 determines that the "event motion" occurs, processing of recognizing a motion which is not the "event motion" is not executed is also applicable to a motion recognition processing unit which does not recognize an "event motion".

Hereinafter, a physical configuration according to the first embodiment of the present invention will be described.

Although a configuration of the mobile telephone of the user on which the acceleration sensor is mounted has the entire motion recognizing system 10 has been described with the above example, the physical configuration is not limited to this. Another possible configuration may also be a configuration where, for example, only the sensor acquiring/storage unit 1 of the configurations illustrated in FIG. 6 is provided in the mobile telephone, and the event motion detecting unit 3 and the recognition processing unit 2 are an external server apparatus or a user's personal computer which performs motion recognition by communicating with the mobile telephone. In this regard, the sensor data acquiring/storage unit 1 has a communication function of transmitting sensor data to the external server apparatus. In this regard, sensor data may be transmitted in real time to execute motion recognition processing, or a memory device may be provided in the server apparatus and recognition processing may be collectively executed when a certain amount of sensor data is acquired.

Further, a method of providing a memory device in a mobile telephone, collectively transmitting sensor data to a server apparatus after measurement of data is finished, moving data to a personal computer apparatus through wired connection and using the data is also applicable.

Furthermore, the sensor is not limited to the acceleration sensor mounted on the mobile telephone, and may be a dedicated acceleration sensor device which is attached to a user's body using a band in some cases.

The above physical configuration applies to the other embodiments of the present invention described below likewise.

Next, an operation according to the first embodiment of the present invention will be described with reference to FIGS. 6 to 10.

(Step S1) The sensor data acquiring/storage unit 1 acquires sensor data of a user's motion, and temporarily stores the sensor data.

(Step S2) The peak detecting unit 31 detects a peak in sensor data obtained from the sensor data acquiring/storage unit 1. When there is a peak in the sensor data ("Y" in step S3), peak information is supplied to the peak interval calculating unit 32 and the peak matching determining unit 34. Detection processing is repeatedly executed every time sensor data of a certain time is obtained, and new peak information is supplied to the peak interval calculating unit 32 and the peak matching determining unit 34 every time the new peak information is obtained. Further, when there is no peak in the obtained sensor data ("N" in step S3), the peak detecting unit 31 does not supply peak information to the peak interval calculating unit 32 and the peak matching determining unit 34 and the operation returns to step S1.

(Step S4) The peak interval calculating unit 32 receives peak information from the peak detecting unit 31 every time the peak detecting unit 31 obtains new peak information. The peak interval calculating unit 32 calculates a time interval between the temporally latest peak and the temporally second latest peak compared to the latest peak using the supplied peak information, and supplies a value of the calculated peak interval and "peak information" of the latest peak to the peak predicting unit 33.

(Step S5) The peak predicting unit 33 predicts a peak which appears next, and supplies "predicted peak information" to the peak matching determining unit 34.

(Step S6) The peak matching determining unit 34 compares the predicted peak information obtained from the peak predicting unit 33 and peak information of the new peak obtained from the peak detecting unit 31, and checks whether or not the two pieces of peak information match. Further, when a state where, after the "predicted peak information" is obtained from the peak predicting unit 33, and the peak detecting unit 31 detects a new peak or when the peak detecting unit 31 does not detect a new peak for predetermined time duration or more continues, the peak matching determining unit 34 performs processing of determining whether or not the pieces of peak information match. The peak matching determining unit 34 supplies the recognition result as to whether or not the peaks match, the predicted peak information and the latest peak information obtained from the peak detecting unit 31 to the time window start/end time setting unit 21 of the recognition processing unit 2.

(Step S8) The time window start/end setting unit 21 sets a time window start time and a time window end time per recognition target motion according to the recognition result supplied from the peak matching determining unit 34 (step S7), and supplies the set time information to the time window data extracting unit 22.

(Step S9) The time window data extracting unit 22 clips sensor data from the sensor data temporarily stored in the sensor data acquiring/storage unit 1 according to the time window start time and end time per recognition motion. The time window data extracting unit 22 supplies the extracted sensor data to the feature amount calculating unit 23.

(Step S10) The feature amount calculating unit 23 calculates a feature amount which characterizes a motion per recognition motion using the sensor data obtained from the time window data extracting unit 22. The feature amount calculating unit 23 supplies the obtained feature amount to the motion recognizing unit 24.

(Step S11) The motion recognizing unit 24 recognizes a motion in the set time window using the feature amount obtained from the feature amount calculating unit 23.

(Step S12) The recognition result output unit 4 outputs a recognition result to, for example, a display device.

Next, an effect according to the first embodiment of the present invention will be described.

The first embodiment of the present invention provides an effect of reducing a calculation amount of processing of recognizing an event motion. The reason is as follows. Focusing on that cyclicity of sensor data is lost when an "event motion" occurs, processing of recognizing the "event motion" is performed assuming that the "event motion" occurs only when cyclicity is lost. More specifically, when there is a gap between a predicted peak appearance time and a peak time which actually appears, it is recognized that cyclicity of the motion is lost, that is, the "event motion" occurs. Further, recognition processing of setting a time window only at around a time at which the "event motion" is highly likely to occur and calculating a feature amount is performed. Hence, it is not necessary to execute a cycle of setting a time window and performing recognition processing, and then setting a new time window by shifting a time window start time by a short time and performing the recognition processing again with respect to all items of obtained sensor data. Consequently, it is possible to reduce the number of times of execution of the recognition processing, and reduce the entire calculation amount of processing of recognizing the "event motion".

Next, a second embodiment of the present invention will be described in details with reference to FIGS. 11 to 13.

Figure 11:
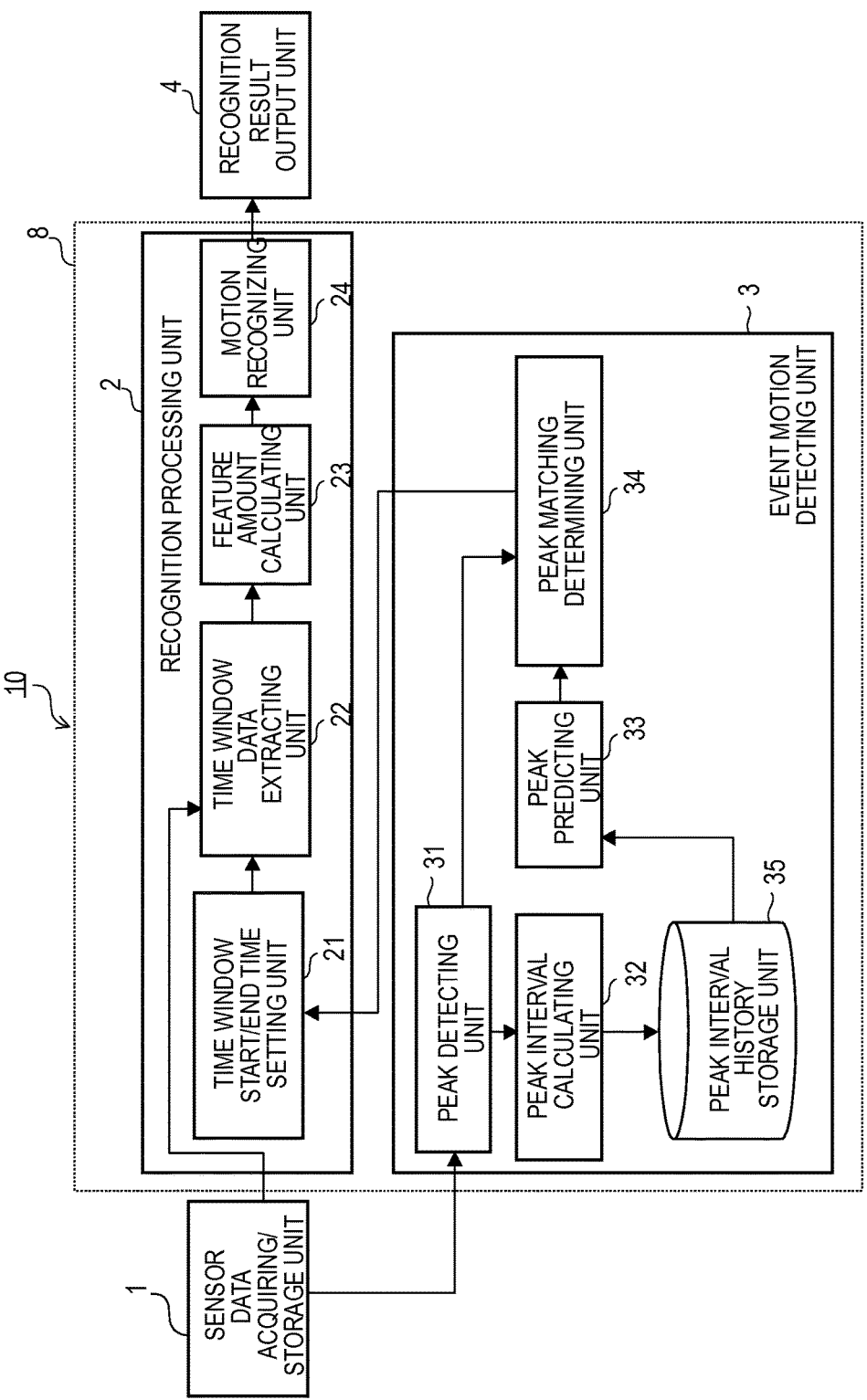
FIG. 11 A figure illustrates a block diagram illustrating a configuration according to a second embodiment of the present invention.

In view of FIG. 6 illustrating the configuration according to the first embodiment and FIG. 11, the second embodiment of the present invention differs from the first embodiment in including a peak interval history storage unit 35.

According to the first embodiment, a peak interval calculating unit 32 calculates a peak interval using peak information of the latest time and peak information of the second latest time obtained from a peak detecting unit 31, and the peak predicting unit 33 predicts a peak which appears next using a value of the latest peak interval obtained in this way. According to the second embodiment, the value of the peak interval calculated by the peak interval calculating unit 32 and peak information of the latest peak are supplied to the peak interval history storage unit 35.

The peak interval history storage unit 35 stores a predetermined number of past 300 peaks of values of peak intervals and detected past peak information of a predetermined time such as past 5 minutes obtained from the peak interval calculating unit 32. The stored values of the peak intervals and peak information are supplied to the peak predicting unit 33. History information to be supplied to the peak predicting unit 33 is determined as history information of past 5 seconds or five pieces of past history information.

FIG. 12 illustrates an example of peak information stored in the peak interval history storage unit 35. FIG. 12 illustrates that the peak interval history storage unit 35 stores 300 pieces of past peak information and 300 values of past peak intervals. The peak interval history storage unit 35 supplies 5 values of the latest peak intervals of $PI_0$ to $PI_{-4}$ and five pieces of the latest peak information of $P_0$ to $P_{-4}$ to the peak predicting unit 33.

The peak predicting unit 33 predicts a peak which appears next from values of peak intervals and peak information of certain time duration obtained from the peak interval history storage unit 35.

A method of predicting a peak is, for example, a method of setting as an appearance time of a predicted peak a value obtained by adding a value of $PI_{ave}$ which is an average value of past peak intervals stored in the peak interval history storage unit 35 to a time $t_0$ of the latest peak $P_0$ instead of adding a value of $PI_0$ which is an immediate peak interval to time $t_0$ of the latest peak $P_0$ as illustrated in FIG. 8B.

A case will be described as a specific example where five values of the latest peak intervals and five pieces of the latest peak information of peak history information illustrated in FIG. 12 will be described. In this regard, an average value of the five values of the past peak intervals is 1.06 second, and time 1.06 second obtained by adding the latest peak $P_0$ to time 0.0 second is a predicted peak time.

Another method is, for example, a method of calculating a maximum value and a minimum value of the values of the peak intervals stored in the peak interval history storage unit 35, and adopting as a peak interval a section in which the number of peak intervals which belongs to each section is the highest as a result of allocating the stored values of the peak intervals to sections obtained by dividing a section between the maximum value and the minimum value by 10.

More specifically, the peak intervals stored in the peak interval history storage unit 35 are $PL_{-n}, PL_{-(n-1)}, \ldots, PL_{-1}$, and $PI_0$ in order of older time, and a peak interval of a minimum value is 0.7 seconds and a peak interval of a maximum value is 1.7 seconds. Meanwhile, ten sections include a section of 0.7 second or more and 0.8 second or less and a section of 1.6 second or more and 1.7 second or less, and each peak interval of $PL_{-n}, PI_{-(n-1)}, \ldots, PL_{-1}$, and $PI_0$ is allocated to each section to which each peak interval belongs. As a result, when, for example, the number of peak intervals which belong to the section of 1.1 second or more and 1.2 second or less is the greatest, a method of setting as a predicted peak occurrence section a section of time 1.1 second to time 1.2 second obtained by adding this section to time 0 second of the peak $P_0$ is applicable.

Subsequent operations of the event motion detecting unit 3 and the recognition processing unit 2 are the same as those of the first embodiment of the present invention, and therefore will not be described.

Further, as described in the first embodiment of the present invention, a method of predicting at the peak predicting unit 33 a more correct peak using not only time information of a peak but also a degree of a value of a data point which is a peak as peak information and a value of an inclination between the data point which is the peak and preceding and subsequent data points may also be applicable. Furthermore, a method of predicting a time having certain time duration without uniformly determining a time at which the peak appears is also applicable. Still further, a statistical predicting method such as a least-square method or curve interpolation is also applicable to a history of peak information and a history of peak intervals.

Next, an operation according to the second embodiment of the present invention will be described in details with reference to FIGS. 11 to 13.

(Step S1) A sensor data acquiring/storage unit 1 acquires sensor data of a user's motion, and temporarily stores the sensor data.

(Step S2) The peak detecting unit 31 detects a peak in the sensor data obtained from the sensor acquiring/storage unit 1. When there is a peak ("Y" in step S3), peak information is supplied to the peak interval calculating unit 32 and the peak matching determining unit 34. Detection processing is repeatedly executed every time sensor data of a certain time is obtained, and new peak information is supplied to the peak interval calculating unit 32 and the peak matching determining unit 34 every time the new peak information is obtained. Further, when there is no peak in the obtained sensor data ("N" in step S3), the peak detecting unit 31 does not supply the peak information to the peak interval calculating unit 32 and the peak matching determining unit 34 and the operation returns to step S1.

(Step S4) The peak interval calculating unit 32 receives the peak information from the peak detecting unit 31 every time the peak detecting unit 31 obtains the new peak information. The peak interval calculating unit 32 calculates a time interval between the temporally latest new peak and the temporally second latest peak compared to the latest peak using the supplied peak information, and supplies the calculated value of the peak interval and "peak information" of the latest peak to the peak interval history storage unit 35.

(Step S13) The peak interval history storage unit 35 stores the value of the peak interval and peak information of the temporally latest peak obtained from the peak interval calculating unit 32.

(Step S5) The peak predicting unit 33 predicts a peak which appears next using a history of values of past peak intervals and past peak information obtained from the peak interval history storage unit 35, and supplies "predicted peak information" to the peak matching determining unit 34.

(Step S6) The peak matching determining unit 34 obtains predicted peak information from the peak predicting unit 33. When the peak detecting unit 31 detects a peak of a new time instead of peak information used by the peak interval calculating unit 32 and the peak predicting unit 33, the detected peak information is obtained from the peak detecting unit 31. The predicted peak information obtained from the peak predicting unit 33 in this way and the new peak information obtained from the peak detecting unit 31 are compared to check whether or not two pieces of peak information match.

When a state where, after the predicted peak information is obtained from the peak predicting unit 33, the peak detecting unit 31 detects a peak of a new time or the peak detecting unit 31 does not detect a new peak for predetermined time duration or more continues, the peak matching determining unit 34 performs processing of determining whether or not pieces of peak information match. The peak matching determining unit 34 supplies a recognition result as to whether or not the peaks match, the predicted peak information and the new peak information obtained from the peak detecting unit 31, to a time window start/end time setting unit 21.

(Step S8) The time window start/end setting unit 21 sets a time window start time and a time window end time per recognition target motion according to the recognition result supplied from the peak matching determining unit 34 (step S7), and supplies the set time information to a time window data extracting unit 22.

(Step S9) The time window data extracting unit 22 clips sensor data from the sensor data temporarily stored in the sensor data acquiring/storage unit 1 according to the time window start time and end time per recognition motion. The time window data extracting unit 22 supplies the extracted sensor data to a feature amount calculating unit 23.

(Step S10) The feature amount calculating unit 23 calculates a feature amount which characterizes a motion per recognition motion using the sensor data obtained from the time window data extracting unit 22. The feature amount calculating unit 23 supplies the obtained feature amount to a motion recognizing unit 24.

(Step S11) The motion recognizing unit 24 recognizes a motion in the set time window using the feature amount obtained from the feature amount calculating unit 23.

(Step S12) A recognition result output unit 4 outputs a recognition result to, for example, a display device.

Next, an effect according to the second embodiment of the present invention will be described.

According to the first embodiment of the present invention, the peak predicting unit 33 predicts a peak which appears next using a value of a peak interval calculated using peak information of an occurrence time of the latest peak and peak information of the second latest time. Meanwhile, according to the second embodiment of the present invention, the peak predicting unit 33 predicts a peak which appears next using values of past peak intervals and past peak information of a certain time stored in the peak interval history storage unit 35. Thus, it is possible to more precisely predict a peak which appears next by using a history of a past certain time. Consequently, compared to the first embodiment of the present invention, it is possible to more adequately set a time window start/end time of "event motion" recognition processing and precisely perform "event motion" recognition processing.

Next, a third embodiment of the present invention will be described with reference to FIGS. 14 to 16.

Figure 14:
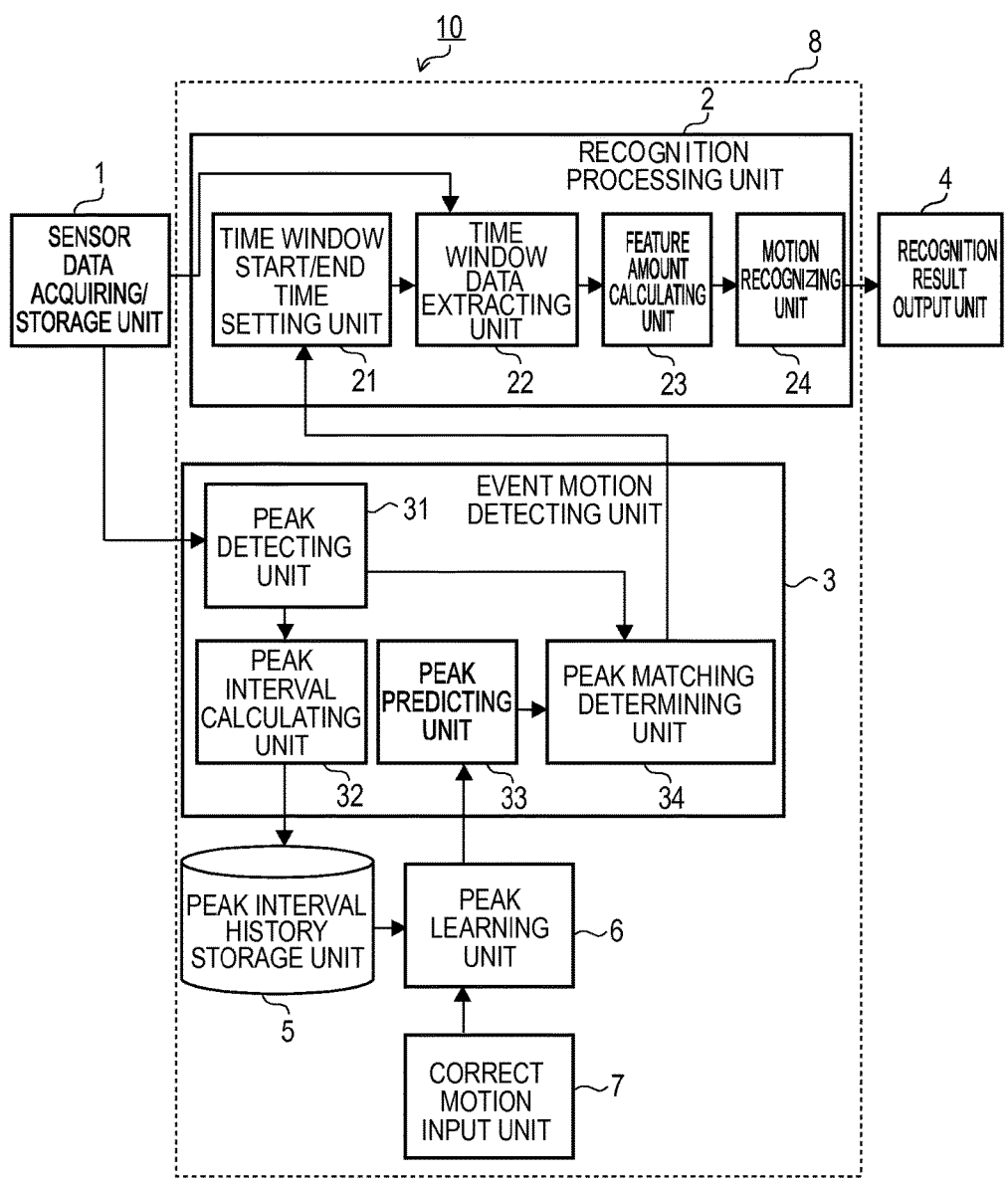
FIG. 14 A figure illustrates a block diagram illustrating a configuration according to a third embodiment of the present invention.

FIG. 14 illustrates a configuration according to the third embodiment of the present invention. Compared to the first embodiment of the present invention illustrated in FIG. 6, a difference is that a peak interval history storage unit 5, a peak learning unit 6 and a correct motion input unit 7 are added.

The peak interval history storage unit 5 stores values of peak intervals and detected past peak information of a predetermined time such as past 24 hours or past one week obtained from a peak interval calculating unit 32.

The correct motion input unit 7 inputs a type of a motion which is actually performed by a user, to the peak learning unit 6. The information to be inputted to the peak learning unit 6 includes at least information of a time at which a motion is performed and information of the type of the motion. Information including at least the information of a time at which a motion is performed and information of the type of the motion is referred to as "correct motion information" in this description. An input method is, for example, a method of inputting a combination of a given time in the past and a type of a motion performed at this time by the user through a computer apparatus or a mobile telephone.

The peak learning unit 6 learns peak information or a peak interval using values of peak intervals and peak information of a certain time stored in the peak interval history storage unit 5 and "correct motion information" obtained from the correct motion input unit 7. As a result of learning, the peak learning unit 6 supplies a parameter used for peak prediction to a peak predicting unit 33. A parameter to be supplied is, for example, a value of a predicted peak occurrence section set by the peak predicting unit 33.

Figures 15A, 15B, 15C:
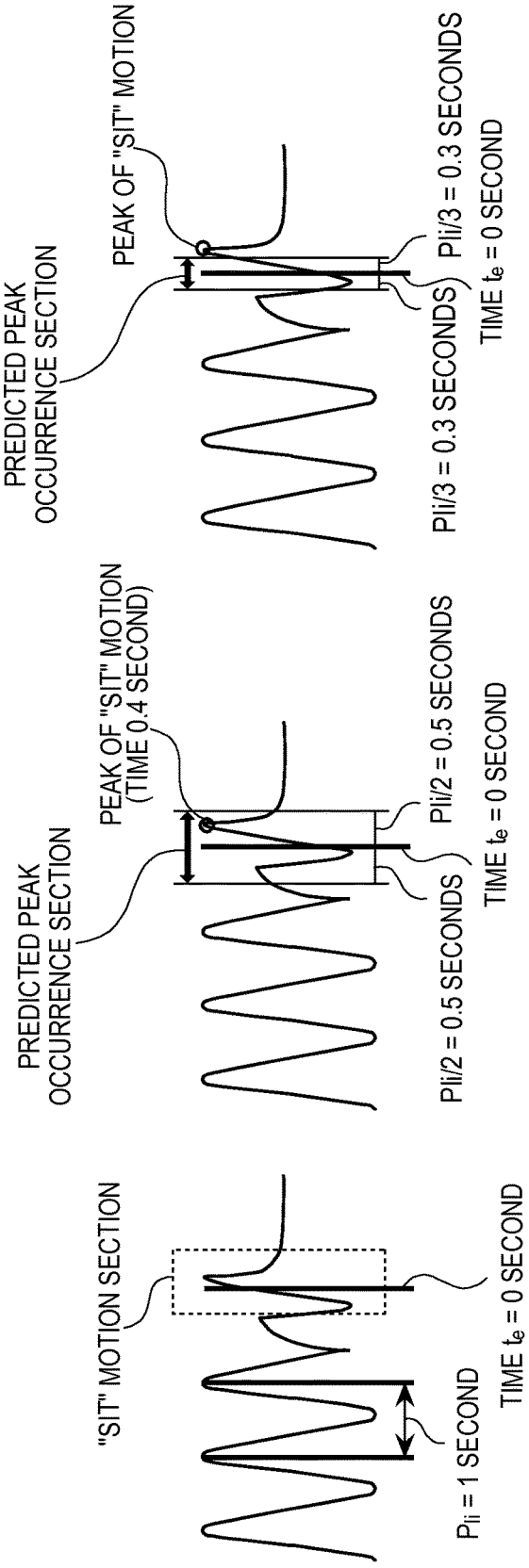
FIG. 15 A figure illustrates a view for explaining learning processing according to the third embodiment of the present invention.

Changing a peak predicting method by way of learning will be described using FIG. 15. As illustrated in FIG. 15A, a case will be described where correct motion information that a "sit" motion which is an "event motion" occurs at a given time in the past. Meanwhile, when the time at which the "sit" motion occurs is 0 second, the peak learning unit 6 obtains a value of a peak interval in a predetermined section of past 5 minutes including time 0 second, and peak information from the peak interval history storage unit 5. Thus, the peak learning unit 6 determines whether or not the "event motion" occurs in a section around time 0 second at which the peak interval and peak information are obtained.

A method of determining that the "event motion" occurs adopts the same processing as those of the peak predicting unit 33 and a peak matching determining unit 34, and obtains peak information from the peak interval history storage unit 5. A case will be described as an example where whether or not peaks match is determined using a predicted peak occurrence section having duration as described in the first embodiment of the present invention.

When, for example, a time $t_0$ second of a latest peak $P_0$ is not included, a peak interval PIi immediately before time 0 second is PIi=1 second and an occurrence time $t_e$ of a predicted peak is time $t_e$=0 second, a section including durations of PIi/2=0.5 seconds prior to and subsequent to time $t_e$=0 second based on time $t_e$=0 second is a predicted peak occurrence time.

Further, whether or not peaks match is determined depending on whether or not a new peak obtained from the peak interval history storage unit 5 is in this predicted peak occurrence section. As a result, when it is determined that an "event motion" occurs at time $t_e$=0 second as in correction information, the peak learning unit 6 does not perform learning and processing is finished.

Meanwhile, unlike the correct motion information, when it is determined that the "event motion" does not occur at time $t_e$=0 second, that is, when a peak is actually detected in a predicted peak occurrence section, a predicted peak occurrence section is set more than necessary. In this case, as illustrated in FIG. 15C, for example, PIi/3=0.3 seconds prior to and subsequent to a section as a conventional predicted peak occurrence section which is shorter than preceding and subsequent PIi/2=0.5 second is a predicted peak occurrence section. The peak learning unit 6 supplies a value of an occurrence section duration used to predict a new peak obtained in this way, to the peak predicting unit 33.

Further, even when information of a motion which is not an "event motion" such as "walk" as correct motion information, the same learning method is applicable. When, for example, correction motion information that a "walk" motion is performed at time t=0 second is obtained, occurrence of an "event motion" is determined in a section around time t=0 second similar to the above-described method. As a result, when it is determined that the "event motion" does not occur at around time t=0 second as indicated by correct motion information, the peak learning unit 6 does not perform learning and processing is finished.

Meanwhile, unlike the correct motion information, when it is determined that the "event motion" occurs, a predicted peak occurrence section is set short more than necessary, preceding and subsequent PIi×(2/3) (second) which is a section as a conventional section which is longer than preceding and subsequent PIi/2 (second) is a predicted peak occurrence section.

Further, the above-described method and, in addition, a newly set peak predicting method may also be a method of verifying whether or not it is possible to correctly determine occurrence of an "event motion". That is, the correct motion information at time t is learned according to the same method as that described above, and learning is performed using a new peak predicting method obtained from the correct motion information again at same time t after a value of a parameter of new peak prediction is obtained. Thus, by repeating learning processing until it is possible to determine an occurrence of an "event motion" as indicated by correct motion information, it is possible to more precisely set a predicted peak occurrence section.

Further, even when the learning processing is repeated, an occurrence of an "event motion" could not be determined as indicated by the correct motion information in some cases, and therefore a rule that an upper limit is set to the number of times of repetition of the learning processing and the learning processing is finished when the number of times of the learning processing reaches the upper limit may be additionally provided.

Furthermore, when a predicted peak occurrence section is changed by way of learning and, in addition, when, for example, a value of a peak and information of an inclination prior to and subsequent to the peak are used for peak prediction as described in the first embodiment of the present invention, learning can be performed according to the same method.

In addition, although a case has been described above where the user specifies time t as correct motion information, an occurrence time of an "event motion" is actually short, and an occurrence time of a correct motion specified by the user relying on user's memory and a time at which the "event motion" actually occurs do not necessarily match in some cases. Hence, the peak interval history storage unit 5 may supply a peak interval of a section having predetermined time duration such as 5 minutes prior to and subsequent to specified time t, and peak information to the peak learning unit 6 to perform learning processing depending on whether or not occurrence of the "event motion" can be determined as indicated by correct motion information in this section.

The peak predicting unit 33 predicts a peak using a parameter which is obtained from the peak learning unit 6 and which is used to predict a new peak.

Hereinafter, a physical configuration according to the third embodiment of the present invention will be described. A possible configuration is a configuration where, for example, the correct motion input unit 7 is a mobile telephone of a user, and the peak interval history storage unit 5 and the peak learning unit 6 are external server apparatuses. Further, the physical configuration is not limited to this and may also be a configuration where, for example, the correct motion input unit 7, the peak interval history storage unit 5 and the peak learning unit 6 are external computer apparatuses, learning processing is performed inside a computer apparatus using correct motion information inputted by the user through the computer apparatus, and a newly obtained peak predicting method is transmitted to the mobile telephone through the computer apparatus to update the predicting method of the peak predicting unit 33 of an event motion detecting unit 3 mounted on the mobile telephone.

Next, an operation according to the third embodiment of the present invention will be described in details with reference to FIGS. 14 and 16.

Figure 16:
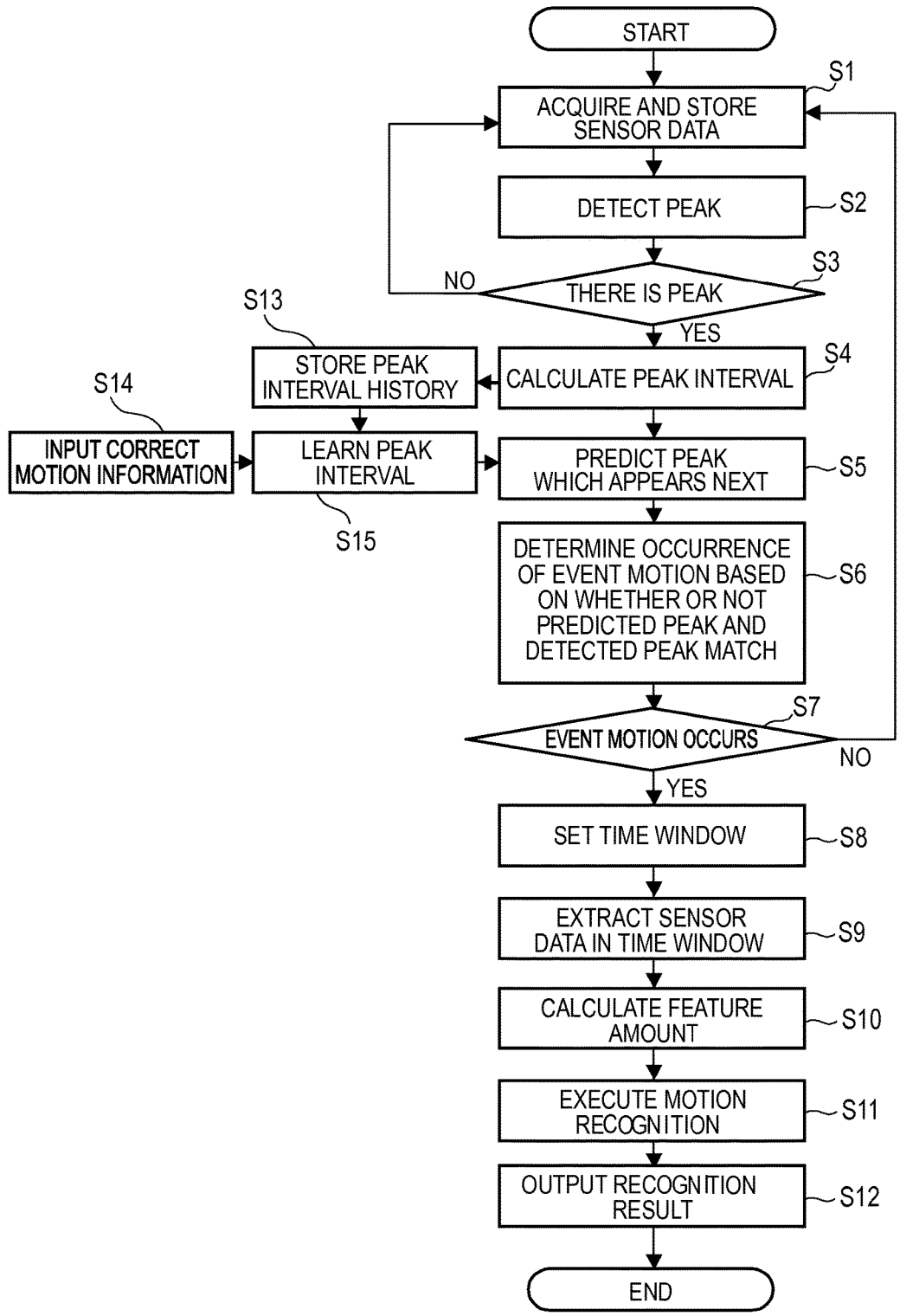
FIG. 16 A figure illustrates a flowchart illustrating processing content according to the third embodiment of the present invention.

The steps represented by S1 to S12 in FIG. 16 are the same operations as S1 to S12 described as to the operation according to the first embodiment of the present invention and therefore will not be described.

(step S13) The peak interval history storage unit 5 stores values of peak intervals and peak information of the temporally latest peak obtained from the peak interval calculating unit 32.

(Step S14) A correct motion input unit 7 inputs correct motion information including the type of a motion which is actually performed by the user and time information of this motion, to the peak learning unit 6.

(Step S15) The peak learning unit 6 learns an inclination of a peak interval using values of peak intervals and peak information of a certain time stored in the peak interval history storage unit 5 and the correct motion information obtained from the correct motion input unit 7. A new peak predicting method obtained by learning is supplied to the peak predicting unit 33.

Learning processing described in step S15 is triggered by an input of correct motion information described in step S14. In this regard, step S14 and step S15 do not need to be executed at the same time, and, after the correct motion information is inputted as described in step S14, a method of performing learning processing at a predetermined time once a day as described in step S15 and supplying an obtained peak predicting method to the peak predicting unit 33 is applicable.

Next, an effect according to the third embodiment of the present invention will be described.

While the peak predicting unit 33 predicts a peak which appears next based on a predetermined rule in the first embodiment of the present invention, the peak learning unit 6 performs learning using correct motion information and changes peak predicting and peak matching methods in the third embodiment of the present invention. Thus, a method is changed to a method of more precisely detecting an "event motion" using correct motion information, so that it is possible to perform processing of precisely recognizing the "event motion" compared to the first embodiment of the present invention.

Further, the third embodiment of the present invention can be used in combination with the second embodiment of the present invention to provide both of the effects.

Figure 10:
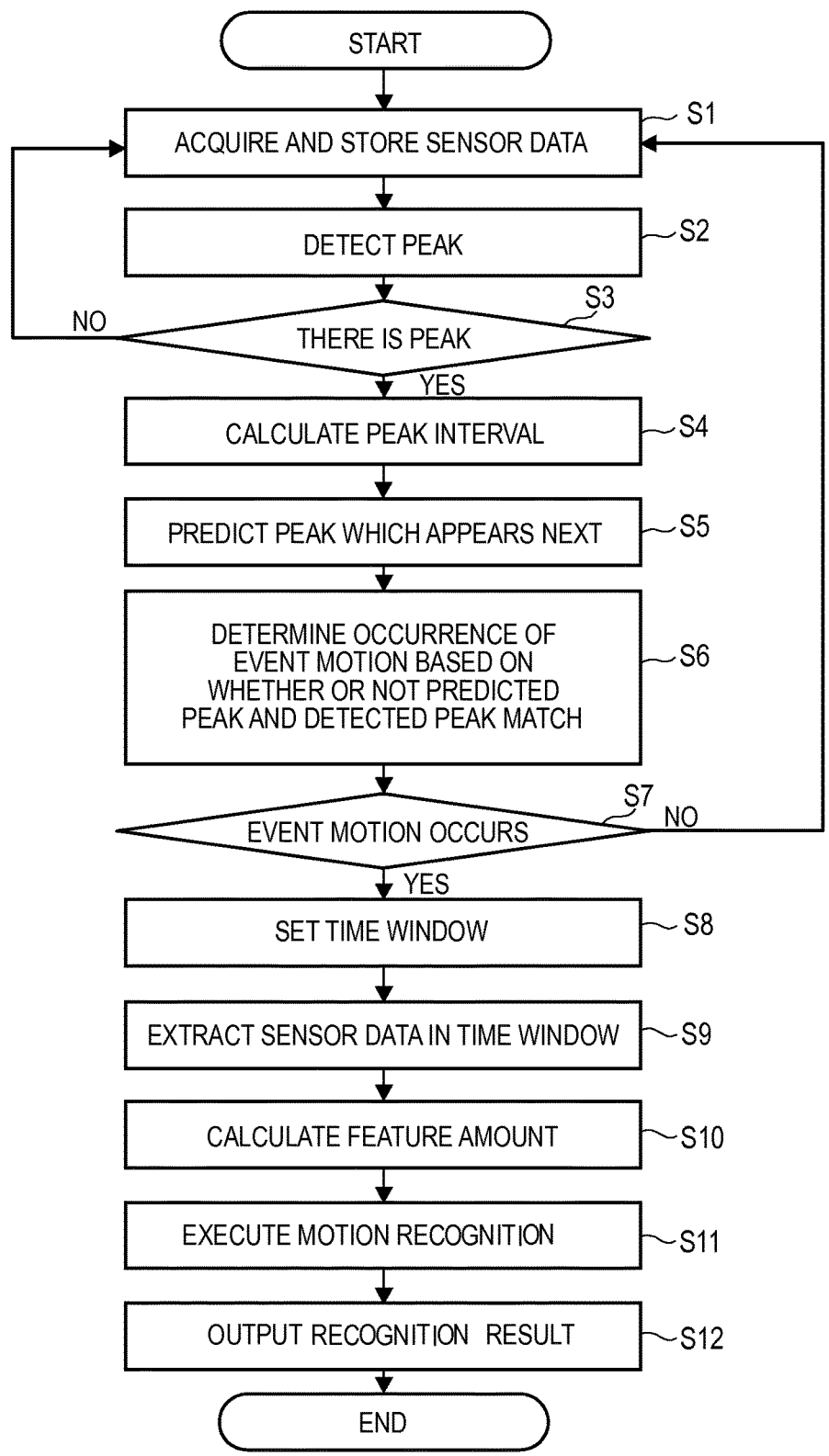
FIG. 10 A figure illustrates a flowchart illustrating processing content according to the first embodiment of the present invention.
Figure 13:
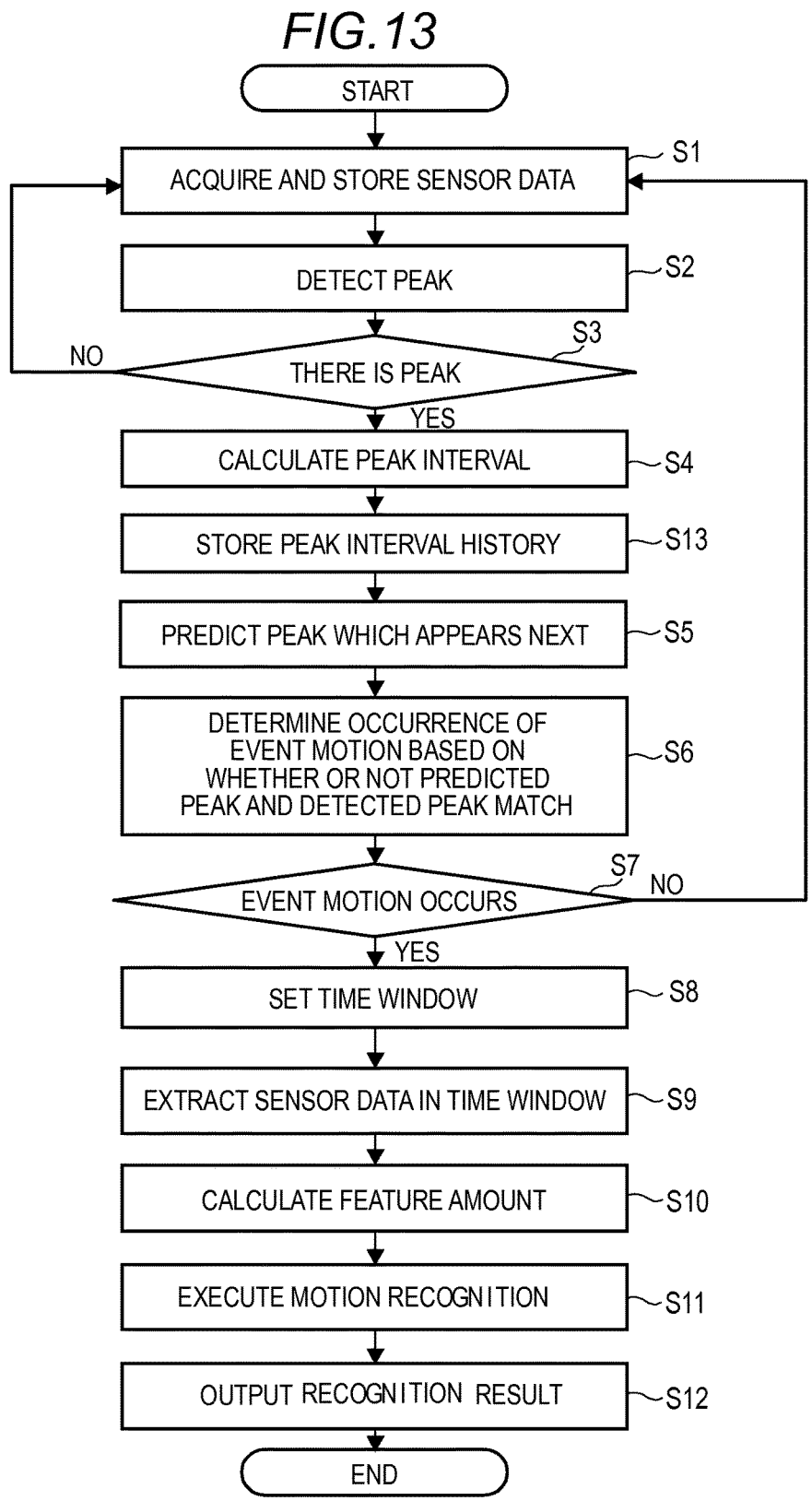
FIG. 13 A figure illustrates a flowchart illustrating processing content according to the second embodiment of the present invention.

Furthermore, a motion recognizing program according to the first to third embodiments of the present invention can be configured as a program which causes a computer to execute part or all of steps illustrated in FIGS. 10, 13 and 16. By installing this program in a computer to execute, it is possible to realize the motion recognizing apparatus and the motion recognizing method according to the first to third embodiments. The computer includes, for example, a server apparatus, a personal computer and a mobile telephone as described above.

Part or entirety of the above embodiments are also described as in the following supplementary notes, and are by no means limited to the below.

(Supplementary Note 1)

A motion recognizing apparatus which recognizes a motion of a user using sensor data has: a cyclicity loss detecting means which detects loss of cyclicity of the sensor data when the user is making the motion; and a recognition processing means which sets a data section used for motion recognition according to the detected loss of the cyclicity of the sensor data, and recognizes the motion of the user based on the sensor data of the data section.

(Supplementary Note 2)

In the motion recognizing apparatus described in Supplementary Note 1, the cyclicity of the sensor data is cyclicity of a peak which is a data point which takes at least a local maximum or a local minimum in the sensor data.

(Supplementary Note 3)

In the motion recognizing apparatus described in Supplementary Note 1 or 2, the data section is set to have predetermined time duration per type of a recognition target operation.

(Supplementary Note 4)

The motion recognition apparatus described in any one of Supplementary Notes 1 to 3 has the recognition processing means intended for each type of a recognition target operation.

(Supplementary Note 5)

In the motion recognizing apparatus described in any one of Supplementary Notes 1 to 4, the sensor data is output data of an acceleration sensor which operates accompanying the motion of the user.

(Supplementary Note 6)

In the motion recognizing apparatus described in any one of Supplementary Notes 1 to 5, the cyclicity loss detecting means has: a peak detecting unit which detects from the sensor data a peak which is a data point which takes at least a local maximum or a local minimum; a peak interval calculating unit which calculates a time interval between peaks from an occurrence time of a plurality of detected peaks; a peak predicting unit which predicts peak information including at least an occurrence time of a next peak using a value of the peak interval calculated by the peak interval calculating unit and an occurrence time of the peak detected by the peak detecting unit; and a peak matching determining unit which determines whether the peak predicted by the peak predicting unit and the peak detected by the peak detecting unit from the sensor data match or not.

(Supplementary Note 7)

The motion recognizing apparatus described in Supplementary Note 6 further has a peak interval history storage unit which stores time information of the peak of a certain past period detected by the peak detecting unit and the peak interval of the certain past period calculated by the peak interval calculating unit, and the peak predicting unit predicts the peak information including at least the occurrence time of the next peak using a history of the peak information and the peak interval stored in the peak interval history storage unit.

(Supplementary Note 8)

The motion recognizing apparatus described in Supplementary Note 6 further has: a peak interval history storage unit which stores time information of the peak of a certain past period detected by the peak detecting unit and the peak interval of the certain past period calculated by the peak interval calculating unit; a correct motion input unit which inputs correct motion information including at least a type of a motion which is actually made and a time at which the motion is made; and a peak learning unit which acquires a history of time information of a peak around the time inputted by the correct motion input unit and the peak interval from the peak interval history storage unit, learns a tendency of the peak interval and changes a cyclicity detecting method based on a learning result.

(Supplementary Note 9)

In the motion recognizing apparatus described in any one of Supplementary Notes 6 to 8, the peak matching determining unit determines whether or not the peak predicted by the peak predicting unit and the peak detected by the peak detecting unit from the sensor data match based on a difference between occurrence times.

(Supplementary Note 10)

In the motion recognizing apparatus described in any one of Supplementary Notes 6 to 8, the peak matching determining unit determines whether the peak predicted by the peak predicting unit and the peak detected by the peak detecting unit from the sensor data match or not based on a difference between occurrence times and a difference between peak values.

(Supplementary Note 11)

A motion recognizing system has: a motion recognizing apparatus described in any one of Supplementary Notes 1 to 10; a sensor data acquiring/storage unit which acquires sensor data outputted from a sensor and temporarily stores the sensor data; and a recognition result output unit which outputs a result of motion recognition performed by the recognition processing unit.

(Supplementary Note 12)

A motion recognizing method of recognizing a motion of a user using sensor data includes: a step of detecting loss of cyclicity of the sensor data when the user is making the motion; and a step of setting a data section used for motion recognition according to the detected loss of the cyclicity of the sensor data, and recognizing the motion of the user based on the sensor data of the data section.

(Supplementary Note 13)

In the motion recognizing method described in Supplementary Note 12, the step of detecting the loss of the cyclicity includes: a step of detecting from the sensor data a peak which is a data point which takes at least a local maximum or a local minimum; a step of calculating a time interval between peaks from an occurrence time of a plurality of detected peaks; a step of predicting peak information including at least an occurrence time of a next peak using a value of the calculated peak interval and an occurrence time of the detected peak; and a step of determining whether or not the predicted peak and the detected peak match.

(Supplementary Note 14)

The motion recognizing method described in Supplementary Note 13 further includes a step of storing time information of the detected peak and the calculated peak interval of a certain past period, and the predicting step includes predicting the peak information including at least the occurrence time of the next peak using a history of the stored peak information and peak interval.

(Supplementary Note 15)

The motion recognizing method described in Supplementary Note 13, further includes: a step of storing time information of the detected peak and the calculated peak interval of a certain past period; a step of inputting correct motion information including at least a type of a motion which is actually made and a time at which the motion is made; and a step of acquiring a history of time information of a peak around the inputted time and the peak interval from information in which the time information and the peak interval of the certain past period are stored, learning a tendency of the peak interval and changing a cyclicity detecting method based on a learning result.

(Supplementary Note 16)

In the motion recognizing method described in any one of Supplementary Notes 13 to 15, the determining step includes determining whether or not the predicted peak and the peak detected from the sensor data match based on a difference between occurrence times.

(Supplementary Note 17)

In the motion recognizing method described in any one of Supplementary Notes 13 to 15, the determining step includes determining whether or not the predicted peak and the peak detected from the sensor data match based on a difference between occurrence times and a difference between peak values.

(Supplementary Note 18)

A motion recognizing program of recognizing a motion of a user using sensor data causes a computer to execute: a function of detecting loss of cyclicity of the sensor data when the user is making the motion; and a function of setting a data section used for motion recognition according to the detected loss of the cyclicity of the sensor data, and recognizing the motion of the user based on the sensor data of the data section.

(Supplementary Note 19)

In the motion recognizing program described in any one of Supplementary Note 18, the function of detecting the loss of the cyclicity includes: a function of detecting from the sensor data a peak which is a data point which takes at least a local maximum or a local minimum; a function of calculating a time interval between peaks from an occurrence time of a plurality of detected peaks; a function of predicting peak information including at least an occurrence time of a next peak using a value of the calculated peak interval and an occurrence time of the detected peak; and a function of determining whether or not the predicted peak and the detected peak match.

(Supplementary Note 20)

The motion recognizing program described in Supplementary Note 18 further causes the computer to execute a function of storing time information of the detected peak and the calculated peak interval of a certain past period, and the predicting function includes predicting the peak information including at least the occurrence time of the next peak using a history of the stored peak information and peak interval.

(Supplementary Note 21)

The motion recognizing program described in Supplementary Note 19 further causes the computer to execute: a function of storing time information of the detected peak and the calculated peak interval of a certain past period; a function of inputting correct motion information including at least a type of a motion which is actually made and a time at which the motion is made; and a function of acquiring a history of time information of a peak around the inputted time and the peak interval from information in which the time information and the peak interval of the certain past period are stored, learning a tendency of the peak interval and changing a cyclicity detecting method based on a learning result.

This application claims priority to Japanese Patent Application No. 2012-046610 filed on Mar. 2, 2012, the entire contents of which are incorporated by reference herein.

Although the present invention has been described above with reference to the embodiments, the present invention is by no means limited to the above embodiments. The configurations and the details of the present invention can be variously changed within a scope of the present invention which one of ordinary skill in art can understand.

INDUSTRIAL APPLICABILITY

According to the present invention, by precisely calculating calorie consumption and recording a motion recognition result of one day using, for example, a result obtained by recognizing a motion of a person, a user can use a record as an automatically generated diary when the user browses the record and, in addition, apply the present invention to observe infants or the elderly from a distant place by monitoring an occurrence of a dangerous motion such as "falling" in real time.

REFERENCE SINGS LIST

1 SENSOR DATA ACQUIRING/STORAGE UNIT
2 RECOGNITION PROCESSING UNIT
21 TIME WINDOW START/END TIME SETTING UNIT
22 TIME WINDOW DATA EXTRACTING UNIT
23 FEATURE AMOUNT CALCULATING UNIT
24 MOTION RECOGNIZING UNIT
3 EVENT MOTION DETECTING UNIT

31 PEAK DETECTING UNIT
32 PEAK INTERVAL CALCULATING UNIT
33 PEAK PREDICTING UNIT
34 PEAK MATCHING DETERMINING UNIT
35 PEAK INTERVAL HISTORY STORAGE UNIT
4 RECOGNITION RESULT OUTPUT UNIT
5 PEAK INTERVAL HISTORY STORAGE UNIT
6 PEAK LEARNING UNIT
7 CORRECT MOTION INPUT UNIT
8 MOTION RECOGNIZING APPARATUS
10 MOTION RECOGNIZING SYSTEM

What is claimed is:

1. A motion recognizing apparatus that recognizes a motion of a user using sensor data, comprising:
   a cyclicity loss detecting unit configured to detect loss of cyclicity of the sensor data when the user is making the motion; and
   a recognition processing unit configured to set a data section used for motion recognition according to the detected loss of the cyclicity of the sensor data, and to recognize the motion of the user based on the sensor data of the data section.

2. The motion recognizing apparatus according to claim 1, wherein the cyclicity of the sensor data is cyclicity of a peak which is a data point which takes at least a local maximum or a local minimum in the sensor data.

3. The motion recognizing apparatus according to claim 1, wherein the data section is set to have predetermined time duration per type of a recognition target operation.

4. The motion recognition apparatus according to claim 1, comprising the recognition processing unit intended for each type of a recognition target operation.

5. The motion recognizing apparatus according to claim 1, wherein the sensor data is output data of an acceleration sensor that operates accompanying the motion of the user.

6. The motion recognizing apparatus according to claim 1, wherein the cyclicity loss detecting unit comprises:
   a peak detecting unit configured to detect from the sensor data a peak which is a data point which takes at least a local maximum or a local minimum;
   a peak interval calculating unit configured to calculate a time interval between peaks from an occurrence time of a plurality of detected peaks;
   a peak predicting unit configured to predict peak information including at least an occurrence time of a next peak using a value of the peak interval calculated by the peak interval calculating unit and an occurrence time of the peak detected by the peak detecting unit; and
   a peak matching determining unit configured to determine whether the peak predicted by the peak predicting unit and the peak detected by the peak detecting unit from the sensor data match or not.

7. The motion recognizing apparatus according to claim 6, further comprising a peak interval history storage unit configured to store time information of the peak of a certain past period detected by the peak detecting unit and the peak interval of the certain past period calculated by the peak interval calculating unit, wherein the peak predicting unit predicts the peak information including at least the occurrence time of the next peak using a history of the peak information and the peak interval stored in the peak interval history storage unit.

8. The motion recognizing apparatus according to claim 6, further comprising:
   a peak interval history storage unit configured to store time information of the peak of a certain past period detected by the peak detecting unit and the peak interval of the certain past period calculated by the peak interval calculating unit;
   a correct motion input unit configured to input correct motion information including at least a type of a motion which is actually made and a time at which the motion is made; and
   a peak learning unit configured to acquire a history of time information of a peak around the time inputted by the correct motion input unit and the peak interval from the peak interval history storage unit, learn a tendency of the peak interval and change a cyclicity detecting method based on a learning result.

9. The motion recognizing apparatus according to claim 6, wherein the peak matching determining unit determines whether the peak predicted by the peak predicting unit and the peak detected by the peak detecting unit from the sensor data match or not based on a difference between occurrence times.

10. The motion recognizing apparatus according to claim 6, wherein the peak matching determining unit determines whether the peak predicted by the peak predicting unit and the peak detected by the peak detecting unit from the sensor data match or not based on a difference between occurrence times and a difference between peak values.

11. A motion recognizing system comprising:
    a motion recognizing apparatus according to claim 1;
    a sensor data acquiring/storage unit configured to acquire sensor data outputted from a sensor and temporarily store the sensor data; and
    a recognition result output unit configured to output a result of motion recognition performed by the recognition processing unit.

12. A motion recognizing method of recognizing a motion of a user using sensor data, comprising:
    a step of detecting loss of cyclicity of the sensor data when the user is making the motion; and
    a step of setting a data section used for motion recognition according to the detected loss of the cyclicity of the sensor data, and recognizing the motion of the user based on the sensor data of the data section.

13. The motion recognizing method according to claim 12, wherein the step of detecting the loss of the cyclicity comprises:
    a step of detecting from the sensor data a peak which is a data point which takes at least a local maximum or a local minimum;
    a step of calculating a time interval between peaks from an occurrence time of a plurality of detected peaks;
    a step of predicting peak information including at least an occurrence time of a next peak using a value of the calculated peak interval and an occurrence time of the detected peak; and
    a step of determining whether or not the predicted peak and the detected peak match.

14. The motion recognizing method according to claim 13, further comprising a step of storing time information of the detected peak and the calculated peak interval of a certain past period, wherein the predicting step comprises predicting the peak information including at least the occurrence time of the next peak using a history of the stored peak information and peak interval.

15. The motion recognizing method according to claim 13, further comprising:
    a step of storing time information of the detected peak and the calculated peak interval of a certain past period;

a step of inputting correct motion information including at least a type of a motion which is actually made and a time at which the motion is made; and a step of acquiring a history of time information of a peak around the inputted time and the peak interval from information in which the time information and the peak interval of the certain past period are stored, learning a tendency of the peak interval and changing a cyclicity detecting method based on a learning result.

16. The motion recognizing method according to claim 13, wherein the determining step comprises determining whether or not the predicted peak and the peak detected from the sensor data match based on a difference between occurrence times.

17. The motion recognizing method according to claim 13, wherein the determining step comprises determining whether the predicted peak and the peak detected from the sensor data match or not based on a difference between occurrence times and a difference between peak values.

18. A non-transitory computer readable medium storing a motion recognizing program of recognizing a motion of a user using sensor data, the program causing a computer to execute:

a function of detecting loss of cyclicity of the sensor data when the user is making the motion; and a function of setting a data section used for motion recognition according to the detected loss of the cyclicity of the sensor data, and recognizing the motion of the user based on the sensor data of the data section.

19. The non-transitory computer readable medium storing the motion recognizing program according to claim 18, wherein the function of detecting the loss of the cyclicity comprises:

a function of detecting from the sensor data a peak which is a data point which takes at least a local maximum or a local minimum;

a function of calculating a time interval between peaks from an occurrence time of a plurality of detected peaks;

a function of predicting peak information including at least an occurrence time of a next peak using a value of the calculated peak interval and an occurrence time of the detected peak; and a function of determining whether or not the predicted peak and the detected peak match.

20. The non-transitory computer readable medium storing the motion recognizing program according to claim 18, further causing the computer to execute a function of storing time information of the detected peak and the calculated peak interval of a certain past period, wherein the predicting function comprises predicting the peak information including at least the occurrence time of the next peak using a history of the stored peak information and peak interval.

* * * * *